US011801311B2

(12) United States Patent
Nelson et al.

(10) Patent No.: US 11,801,311 B2
(45) Date of Patent: Oct. 31, 2023

(54) INHIBITING OR DOWNREGULATING GLYCOGEN SYNTHASE BY CREATING PREMATURE STOP CODONS USING ANTISENSE OLIGONUCLEOTIDES

(71) Applicant: Genzyme Corporation, Cambridge, MA (US)

(72) Inventors: Carol A. Nelson, Westford, MA (US); Bruce M. Wentworth, Northborough, MA (US); Ronald K. Scheule, Hopkinton, MA (US); Timothy E. Weeden, Sturbridge, MA (US); Nicholas P. Clayton, Sudbury, MA (US)

(73) Assignee: GENZYME CORPORATION, Cambridge, MA (US)

( * ) Notice: Subject to any disclaimer, the term of this patent is extended or adjusted under 35 U.S.C. 154(b) by 181 days.

(21) Appl. No.: 16/867,261

(22) Filed: May 5, 2020

(65) Prior Publication Data

US 2021/0030893 A1 Feb. 4, 2021

Related U.S. Application Data

(63) Continuation of application No. 15/990,463, filed on May 25, 2018, now Pat. No. 10,682,423, which is a continuation of application No. 15/313,387, filed as application No. PCT/US2015/032141 on May 22, 2015, now abandoned.

(60) Provisional application No. 62/002,294, filed on May 23, 2014.

(51) Int. Cl.

| | |
|---|---|
| ***C07H 21/02*** | (2006.01) |
| ***C07H 21/04*** | (2006.01) |
| ***A61K 48/00*** | (2006.01) |
| ***C12N 15/113*** | (2010.01) |

(52) U.S. Cl.

CPC .......... *A61K 48/005* (2013.01); *C12N 15/113* (2013.01); *C12N 15/1137* (2013.01); *C12Y 204/01011* (2013.01); *C12N 2310/11* (2013.01); *C12N 2310/3233* (2013.01); *C12N 2310/3513* (2013.01); *C12N 2320/33* (2013.01)

(58) Field of Classification Search

CPC .......................... C12N 15/113; C12N 2310/11
See application file for complete search history.

(56) References Cited

U.S. PATENT DOCUMENTS

| | | | |
|---|---|---|---|
| 5,034,506 | A | 7/1991 | Summerton |
| 5,142,047 | A | 8/1992 | Summerton |
| 5,166,315 | A | 11/1992 | Summerton |
| 5,185,444 | A | 2/1993 | Summerton |
| 5,217,866 | A | 6/1993 | Summerton |
| 5,506,337 | A | 4/1996 | Summerton |
| 5,521,063 | A | 5/1996 | Summerton |
| 5,698,685 | A | 12/1997 | Summerton |
| 2009/0099066 | A1 | 4/2009 | Moulton |
| 2017/0182189 | A1 | 6/2017 | Nelson |
| 2019/0117794 | A1 | 4/2019 | Nelson |

FOREIGN PATENT DOCUMENTS

| | | | | |
|---|---|---|---|---|
| CA | 2691673 | A1 * | 1/2009 | .......... C12N 15/113 |
| WO | 2008036127 | A2 | 3/2008 | |
| WO | 2008036127 | A3 | 11/2008 | |

OTHER PUBLICATIONS

Douillard-Guilloux et al. (Human Molecular Genetics, 2010, 19, 4, 684-696).*
Vickers et al. (The Journal of Biological Chemistry, vol. 278, No. 9, 7108-7118, 2003).*
Clayton et al. (Molecular Therapy—Nucleic Acids, 2014, 3, e206, 1-11).*
Abes, S. et al. (Dec. 1, 2006). "Vectorization of Morpholino Oligomers by the (R-Ahx-R)4 Peptide Allows Efficient Splicing Correction in the Absence of Endosomolytic Agents," J Control Release 116(3):304-313.
Ashe, K.M. et al. (Aug. 1, 2010). "Inhibition of Glycogen Biosynthesis via mTORCI Suppression as an Adjunct Therapy for Pompe disease," Molecular Genetics and Metabolism 100(4):309-315.
Bhuvanagiri, M. et al. (Sep. 15, 2010). "NMD: RNA Biology Meets Human Genetic Medicine," Biochem J. 430(3):365-377.
Clayton, N.P. et al. (Oct. 28, 2014) "Antisense Oligonucleotide-Mediated Suppression of Muscle Glycogen Synthase 1 Synthesis as an Approach for Substrate Reduction Therapy of Pompe Disease," Molecular Therapy Nucleic Acids 3(10):e206, 11 pages.
Douillard-Guilloux, G. et al. (2008, e-pub. Sep. 9, 2008). "Modulation of Glycogen Synthesis by RNA Interference: Towards a New Therapeutic Approach for Glycogenosis Type II", Human Molecular Genetics 17 (24):3876-3886.
Douillard-Guilloux, G. et al. (Dec. 3, 2009). "Restoration of Muscle Functionality by Genetic Suppression of Glycogen Synthesis in a Murine Model of Pompe Disease," Human Molecular Genetics 19(4):684-696. Supplementary figure 1, (Feb. 10, 2010), Retrieved from the Internet: URL:http://hmg.oxfordjournals.org/content/suppl/2009/12/05/ddp535.DC1/ddp535supp.pdf.
Dwi U Kemaladewi et al. (Apr. 20, 2011). "Dual Exon Skipping in Myostatin and Dystrophin for Duchenne Muscular Dystrophy," BMC Medical Genomics 4(1):36.
Fletcher, S. et al. (2007, e-pub. Jun. 19, 2007) "Morpholino Oligomer-Mediated Exon Skipping Averts the Onset of Dystrophic Pathology in the mdx Mouse", Mal Ther. 15(9):1587-1592.

(Continued)

*Primary Examiner* — Amy H Bowman
(74) *Attorney, Agent, or Firm* — Morrison & Foerster LLP

(57) ABSTRACT

The present disclosure relates to antisense oligonucleotides (AONs) for modulating the expression of glycogen synthase. AONs of the present disclosure may be useful in treating diseases associated with the modulation of the expression of the enzyme glycogen synthase, such as Pompe disease. Also provided by the present disclosure are compositions comprising AONs, as well as methods of down regulating mRNA coding for glycogen synthase, methods for reducing glycogen synthase in skeletal and cardiac muscle, and methods for treating Pompe disease.

18 Claims, 13 Drawing Sheets

Specification includes a Sequence Listing.

(56) References Cited

OTHER PUBLICATIONS

International Preliminary Report on Patentability dated Nov. 29, 2016, for PCT Application No. PCT/US2015/032141, filed May 22, 2015, 10 pages.
International Search Report dated Aug. 28, 2015, for PCT Application No. PCT/US2015/032141, filed May 22, 2015, 5 pages.
Moreland, R. et al. (Feb. 2012, e-pub. Jan. 19, 2012). "Pompe Syndrome: Dysregulation of Multiple Facets of Glycogen Metabolism in a Murine Model of Pompe Disease," Molecular Genetics and Metabolism 105(2):S47. Located at: https://www.sciencedirect.com/science/article/abs/pii/S1096719211005336?via%3Dihub.
Park, K.S. et al. (2000). "Induction of Insulin Resistance in Human Skeletal Muscle Cells by Downregulation of Glycogen Synthase Protein Expression," Metabolism 49(8):962-968.
Ward, A.J. et al. (May 14, 2014). "Nonsense-Mediated Decay as a Terminating Mechanism for Antisense Oligonucleotides," Nucleic Acids Research 42(9):5871-5879.
Ward, A.J. et al. (May 14, 2014). "Nonsense-Mediated Decay as a Terminating Mechanism for Antisense Oligonucleotides," Nucleic Acids Research 42(9):5871-5879. Supplementary Data, Mar. 3, 2014, pp. SI-SI5.
Written Opinion of the International Searching Authority dated Aug. 28, 2015, for PCT Application No. PCT/US2015/032141, filed May 22, 2015, 8 pages.
Disterer, P. et al. (2012). "Antisense-Mediated Exon-Skipping To Induce Gene Knockdown," Chapter 19 In Exon Skipping, Humana Press, pp. 289-305.
Siva, K. et al. (Feb. 2014). "Exon-Skipping Anti Sense Oligonucleotides To Correct Missplicing In Neurogenetic Diseases," Nucleic Acid Therapeutics 24(1):69-86.

* cited by examiner

Fig. 1A: SEQ ID NO.: 1

Homo sapiens glycogen synthase 1 (muscle) (GYS1), transcript variant 1, mRNA

NCBI Reference Sequence: NM_002103.4

```
   1 tcctggcggc tgcgaggttt cactgcaggg gcgccagtgg gctcagtgac gctgcggcct
  61 ccttctgcct aggtcccaac gcttcgggc agggtgcgg tcttgcaata ggaagccgag
 121 cgtcttgcaa gcttcccgtc gggcaccagc tactcggccc cgcaccctac ctggtgcatt
 181 ccctagacac ctccggggtc cctacctgga gatccccgga gcccccttc ctgcgccagc
 241 catgccttta aaccgcactt tgtccatgtc ctcactgcca ggactggagg actgggagga
 301 tgaattcgac ctggagaacg cagtgctctt cgaagtggcc tgggaggtgg ctaacaaggt
 361 gggtggcatc tacacggtgc tgcagacgaa ggcgaaggtg acaggggacg aatggggcga
 421 caactacttc ctggtggggc cgtacacgga gcagggcgtg aggacccagg tggaactgct
 481 ggaggccccc accccggccc tgaagaggac actggattcc atgaacagca agggctgcaa
 541 ggtgtatttc gggcgctggc tgatcgaggg aggccctctg gtggtgctcc tggacgtggg
 601 tgcctcagct tgggccctgg agcgctggaa gggagagctc tgggatacct gcaacatcgg
 661 agtgccgtgg tacgaccgcg aggccaacga cgctgtcctc tttggctttc tgaccacctg
 721 gttcctgggt gagttcctgg cacagagtga ggagaagcca catgtggttg ctcacttcca
 781 tgagtggttg gcaggcgttg gactctgcct gtgtcgtgcc cggcgactgc ctgtagcaac
 841 catcttcacc acccatgcca cgctgctggg gcgctacctg tgtgccggtg ccgtggactt
 901 ctacaacaac ctggagaact tcaacgtgga caaggaagca ggggagaggc agatctacca
 961 ccgatactgc atggaaaggg cggcagccca ctgcgctcac gtcttcacta ctgtgtccca
1021 gatcaccgcc atcgaggcac agcacttgct caagaggaaa ccagatattg tgacccccaa
1081 tgggctgaat gtgaagaagt tttctgccat gcatgagttc cagaacctcc atgctcagag
1141 caaggctcga atccaggagt ttgtgcgggg ccatttttat gggcatctgg acttcaactt
1201 ggacaagacc ttatacttct ttatcgccgg ccgctatgag ttctccaaca agggtgctga
1261 cgtcttcctg gaggcattgg ctcggctcaa ctatctgctc agagtgaacg gcagcgagca
1321 gacagtggtt gccttcttca tcatgccagc gcggaccaac aatttcaacg tggaaaccct
1381 caaaggccaa gctgtgcgca aacagctttg ggacacggcc aacacggtga aggaaaagtt
1441 cgggaggaag ctttatgaat ccttactggt tgggagcctt cccgacatga acaagatgct
1501 ggataaggaa gacttcacta tgatgaagag agccatcttt gcaacgcagc ggcagtcttt
1561 ccccccctgtg tgcacccaca atatgctgga tgactcctca gaccccatcc tgaccaccat
1621 ccgccgaatc ggcctcttca atagcagtgc cgacagggtg aaggtgattt tccacccgga
1681 gttcctctcc tccacaagcc ccctgctccc tgtggactat gaggagtttg tccgtggctg
1741 tcaccttgga gtcttcccct cctactatga gccttggggc tacacaccgg ctgagtgcac
1801 ggttatggga atccccagta tctccaccaa tctctccggc ttcggctgct tcatggagga
1861 acacatcgca gacccctcag cttacggtat ctacattctt gaccggcggt tccgcagcct
1921 ggatgattcc tgctcgcagc tcacctcctt cctctacagt ttctgtcagc agagccggcg
1981 gcagcgtatc atccagcgga accgcacgga gcgcctctcc gaccttctgg actggaaata
2041 cctaggccgg tactatatgt ctgcgcgcca catggcgctg tccaaggcct ttccagagca
2101 cttcacctac gagcccaacg aggcggatgc ggcccagggg taccgctacc cacggccagc
2161 ctcggtgcca ccgtcgccct cgctgtcacg acactccagc ccgcaccaga gtgaggacga
2221 ggaggatccc cggaacgggc cgctggagga agacggcgag cgctacgatg aggacgagga
2281 ggccgccaag gaccggcgca acatccgtgc accagagtgg ccgcgccgag cgtcctgcac
2341 ctcctccacc agcggcagca agcgcaactc tgtggacacg gccacctcca gctcactcag
2401 caccccgagc gagcccctca gccccaccag ctccctgggc gaggagcgta actaagtccg
2461 ccccaccaca ctccccgcct gtcctgcctc tctgctccag agagaggatg cagaggggtg
2521 ctgctcctaa accccgctc cagatctgca ctgggtgtgg ccccgcagtg cccccaccca
2581 gtccgccaaa cactccaccc cctccagctc cagtttccaa gttcctgcac tccagaatcc
2641 acaaagccgt gcctttctct ggctccagaa tatgcataat cagcgccctg gagtcccctg
2701 ggcctggacc gcttcccaga ggccaggaat ctgccattac tctgcggtgg tgccagaggt
2761 tttaggaaac ctggcatggt gctttcaggt ctggggcttt tagagccccc cgtgtggctt
2821 acaaattcta cagcatacag agcaggccac gctcaggccc ggcatgcggg ccaccaagtt
2881 ctggaaacca cgtggtgtcc ctgcgaatgg ggcgatcaag tccagagccg ggcactttc
2941 agagtttgaa ggtaactgag agcagatggt cctccatttc aactccagaa gtggggctct
3001 gggagggatg ttctagccct ccctggcatg tcagagccag gctctgcctg gaggatccct
3061 ccatccggct cctgtcatcc cctacacttt ggccaagcaa gaggtggtag aaccacttgg
3121 ctgctcattc cttctggagg acacacagtc tcagtccaga tgccttcctg tctttctggc
3181 cctttctgga ccagatccta ctcttccttt ctaaatctga gatctccctc cagggaatcc
3241 gcctgcagag gacagagctg gctgtcttcc cccaccccta acctggctta ttcccaactg
```

Fig. 1A: SEQ ID NO.: 1 CONTINUED

```
3301 ctctgcccac tgtgaaacca ctaggttcta ggtcctggct tctagatctg gaaccttacc
3361 acgttactgc atactgatcc ctttcccatg atccagaact gaggtcactg ggttctagaa
3421 cccccacatt tacctcgagg ctcttccatc cccaaactgt gccctgcctt cagctttggt
3481 gaaagggagg gcccctcatg tgtgctgtgc tgtgtctgca ccgcttggtt tgcagttgag
3541 aggggagggc aggaggggtg tgattggagt gtgtccggag atgagatgaa aaaaatacat
3601 ctatatttaa gaatcccaaa aaaaaaaaaa aaaaa (SEQ ID NO.:1)
```

Fig. 1B: SEQ ID NO.: 2

NCBI Reference Sequence: NM_002103.4 (CDS)

CDS of Homo sapiens glycogen synthase 1 (muscle) (GYS1), transcript var iant 1, mRNA MPLNRTLSMSSLPGLEDWEDEFDLENAVLFEVAWEVANKVGGIY

TVLQTKAKVTGDEWGDNYFLVGPYTEQGVRTQVELLEAPTPALKRTLDSMNSKGCKVY

FGRWLIEGGPLVVLLDVGASAWALERWKGELWDTCNIGVPWYDREANDAVLFGFLTTW

FLGEFLAQSEEKPHVVAHFHEWLAGVGLCLCRARRLPVATIFTTHATLLGRYLCAGAV

DFYNNLENFNVDKEAGERQIYHRYCMERAAAHCAHVFTTVSQITAIEAQHLLKRKPDI

VTPNGLNVKKFSAMHEFQNLHAQSKARIQEFVRGHFYGHLDFNLDKTLYFFIAGRYEF

SNKGADVFLEALARLNYLLRVNGSEQTVVAFFIMPARTNNFNVETLKGQAVRKQLWDT

ANTVKEKFGRKLYESLLVGSLPDMNKMLDKEDFTMMKRAIFATQRQSFPPVCTHNMLD

DSSDPILTTIRRIGLFNSSADRVKVIFHPEFLSSTSPLLPVDYEEFVRGCHLGVFPSY

YEPWGYTPAECTVMGIPSISTNLSGFGCFMEEHIADPSAYGIYILDRRFRSLDDSCSQ

LTSFLYSFCQQSRRQRIIQRNRTERLSDLLDWKYLGRYYMSARHMALSKAFPEHFTYE

PNEADAAQGYRYPRPASVPPSPSLSRHSSPHQSEDEEDPRNGPLEEDGERYDEDEEAA

KDRRNIRAPEWPRRASCTSSTSGSKRNSVDTATSSSLSTPSEPLSPTSSLGEERN

Fig. 2A: SEQ ID NO.: 3

Mus musculus glycogen synthase 1, muscle (Gys1), mRNA

NCBI Reference Sequence: NM_030678.3

```
   1 actgcagctg cccgcccgat tcagtgtctc agctcaccct acctgagtcg gagcgctctg
  61 gggcgggggt gcggtcgtgc aataggaagc ggagcgcctt gcaagcttcc cctgggacac
 121 ccgctaactc taccggtcac caagtctgct gcgttcccag ccgatctctc tggtttccag
 181 ttttggtgct cgaagtcccc tgcccgcagt agccatgcct ctcagccgca gtctctctgt
 241 gtcctcgctt ccaggattgg aagactggga ggatgaattc gaccccgaga acgcagtgct
 301 tttcgaggtg gcctgggagg tggccaacaa ggtgggtggc atctacactg tgctgcagac
 361 gaaggcgaag gtgacagggg atgaatgggg tgacaactac tatctggtgg gaccatacac
 421 ggagcagggt gtgaggacgc aggtagagct cctggagccc ccaactccgg aactgaagag
 481 gactttggat tccatgaaca gcaagggttg taaggtgtat tttgggcgtt ggctgatcga
 541 gggggggacc ctagtggtgc tcctggatgt aggagcctca gcttgggccc tggagcgctg
 601 gaagggtgag ctttgggaca cctgcaacat cggggtaccc tggtacgacc gcgaggccaa
 661 tgacgctgtc ctgttcggct tcctcaccac ctggttcctg ggtgagttcc tggcccagaa
 721 cgaagagaag ccgtatgtgg ttgcccactt ccacgaatgg ttggctggcg ttggtctgtg
 781 tctgtgccgt gcccggcgct tgccggtggc aaccatcttc accactcatg ccacgctgct
 841 ggggcgctac ctgtgtgctg gcgctgtgga cttctacaac aacctggaga atttcaatgt
 901 agacaaggaa gcaggagaga ggcagatcta tcaccggtac tgcatggagc gtgcagcagc
 961 tcactgtgcc catgtcttca ctaccgtatc ccagatcacc gcaatcgagg ctcaacacct
1021 ccttaagaga aaaccagata ttgtgacccc caacgggctg aatgtgaaga agttctctgc
1081 tatgcacgaa ttccagaacc ttcatgctca gagcaaagca cgaatccagg aatttgtgcg
1141 tggccatttt tatgggcacc tggacttcaa cctagacaag actttgtatt tctttatcgc
1201 tggccgctat gagttttcca acaagggagc tgatgtgttc ctggaggcat tggcccggct
1261 caactatctg ctcagagtga atggcagtga gcaaacagtt gtcgcattct tcatcatgcc
1321 ggcccggacc aataatttca acgtggaaac cctgaagggc caagccgtgc gcaaacaact
1381 atgggacaca gccaatacag tcaaggagaa atttgggagg aagctctacg aatccctttt
1441 agtggggagc ctcccggaca tgaacaagat gctggacaag gaggacttca ctatgatgaa
1501 gagagccatc tttgccactc agcggcagtc tttcccacca gtgtgcaccc acaacatgct
1561 ggacgactcc tcagacccca tcttgaccac catccgccga attggccttt tcaacagcag
1621 tgccgaccgt gtgaaggtga tttttcaccc agaattcctt tcttccacaa gccctctcct
1681 ccccgtggat tatgaggaat ttgtccgcgg ctgtcacctt ggggtcttcc cctcctacta
1741 tgagccctgg ggctacacac cagcggagtg cactgtcatg ggcatcccca gcatctccac
1801 caacctctcc ggctttggct gctttatgga ggaacacatc gcagatccct cagcttacgg
1861 catttacatt ctggatcgga ggttccgcag cctggatgat tcatgctcac agctcacctc
1921 cttcctgtac agcttctgcc agcagagccg gcgacagcgc atcatccagc ggaaccgcac
1981 agaacggttg tcggacttgc tagattggaa gtacctgggc cggtactaca tgtctgcgcg
2041 ccacatggct ctggccaagg cctttccaga ccacttcacc tatgaacccc atgaggtaga
2101 tgcgacccag ggtaccggt acccacgacc agcctccgtc ccgccgtcgc cctcactgtc
2161 tcgacactcc agcccacacc agagtgagga tgaggaagag ccacgggatg gacccctggg
2221 ggaagacagt gagcgttatg atgaggaaga ggaggctgcc aaggaccgcc gcaacatccg
2281 ggcacctgag tggccacgca gggcctcctg ttcctcctcc acaggtggca gcaagagaag
2341 caactcggtg gacactgggc cctccagctc actcagcaca cccactgagc ccctgagtcc
2401 taccagttcc ctgggtgagg agcgcaacta agctcccacc cccatcccat tccctgcctg
2461 tccagtgctc ctctcgcaga gggcctatgc agatgggagg gtgcctgaac cccactccag
2521 actcttgagt gggaccccta cccagtgtgg tccatagcct aacctctgtt tcagacactc
2581 cagcccttga gctccaatct tggagttccc gcactccacg ccgccgtgcc tttcttggat
2641 tgcaggatgc attctttgtg cactgatctg gagtctccag gcttagactg ggtcccagag
2701 gccaggcatc tgccattgtt tttcaatgcc agaggtttta ggacacctgg tttattggct
2761 tccaggctgt ggcttcttcg tttgatccta taatcataca gagtatgctt tgctcaggcc
2821 tgcctctggg accacctcat gttggattct gtgtggcttc ccgaatcagc caagttcaga
2881 gttaggacat ttcagggatt aacataattg aaaatcagcc tgcaaggtag ctcagtagct
2941 ctgtcgacag attgcttgtc tagcatgccc gaagccctgg gatctaactc tagaacctca
3001 taaacctggt gcggtgatac acatctgtaa tcccagcact cggtaggtag aggtagacgg
3061 atcaagagtt aaaggccatc atcctctgct acatagggag ttcaaggcca aactgggcaa
3121 catgagacac tgtctcaaaa gcaaagtaaa ggtggtggaa tgctcacggt cctccatttc
```

Fig. 2A: SEQ ID NO.: 3 CONTINUED

```
3181 aacccacgac tgcgatgctg ggacatgctg caaggttggc ctccctgggt gtgttcttca
3241 aaggagcatg cggagttgga ccagacacct ttctgccttt tttctggacc agaccttctt
3301 ttccttggtc cagtgtcccc tctagggaat gcctccattg agggcagaat gtctgtcaac
3361 cccacaagtg ctcagcccac tgtgaaacca ctgggttctg ggtcccagtg gctgaatcag
3421 gagtcttttg tcactgtgct gcaccccggt cccctttcct gatacaaaac cgagcccacc
3481 ggcttcttga agccccacat gtacctcgag gcctttctgc ctgcaagctt cagtgaatgg
3541 gcgggcccct cctcacgtgt gctgtgtctg gcccagtgcc tttggtttgc atttgggagg
3601 gggagggcag aaggtgtgtg attggagtgt gtctagagat gaaaaaaaaa aaaagaaaat
3661 acacctgtat ttaagaatgc c (SEQ ID NO.: 3)
```

Fig. 2B: SEQ ID NO.: 4

NCBI Reference Sequence: NM_030678.3 (CDS)

MPLSRSLSVSSLPGLEDWEDEFDPENAVLFEVAWEVANKVGGIY

TVLQTKAKVTGDEWGDNYYLVGPYTEQGVRTQVELLEPPTPELKRTLDSMNSKGCKVY

FGRWLIEGGPLVVLLDVGASAWALERWKGELWDTCNIGVPWYDREANDAVLFGFLTTW

FLGEFLAQNEEKPYVVAHFHEWLAGVGLCLCRARRLPVATIFTTHATLLGRYLCAGAV

DFYNNLENFNVDKEAGERQIYHRYCMERAAAHCAHVFTTVSQITAIEAQHLLKRKPDI

VTPNGLNVKKFSAMHEFQNLHAQSKARIQEFVRGHFYGHLDFNLDKTLYFFIAGRYEF

SNKGADVFLEALARLNYLLRVNGSEQTVVAFFIMPARTNNFNVETLKGQAVRKQLWDT

ANTVKEKFGRKLYESLLVGSLPDMNKMLDKEDFTMMKRAIFATQRQSFPPVCTHNMLD

DSSDPILTTIRRIGLFNSSADRVKVIFHPEFLSSTSPLLPVDYEEFVRGCHLGVFPSY

YEPWGYTPAECTVMGIPSISTNLSGFGCFMEEHIADPSAYGIYILDRRFRSLDDSCSQ

LTSFLYSFCQQSRRQRIIQRNRTERLSDLLDWKYLGRYYMSARHMALAKAFPDHFTYE

PHEVDATQGYRYPRPASVPPSPSLSRHSSPHQSEDEEEPRDGPLGEDSERYDEEEEAA

KDRRNIRAPEWPRRASCSSSTGGSKRSNSVDTGPSSSLSTPTEPLSPTSSLGEERN (SEQ ID NO.:4)

Gys1 mRNA levels are reduced in skeletal and cardiac muscles of Pompe mice treated with repeated intravenous injections of GS-PPMO
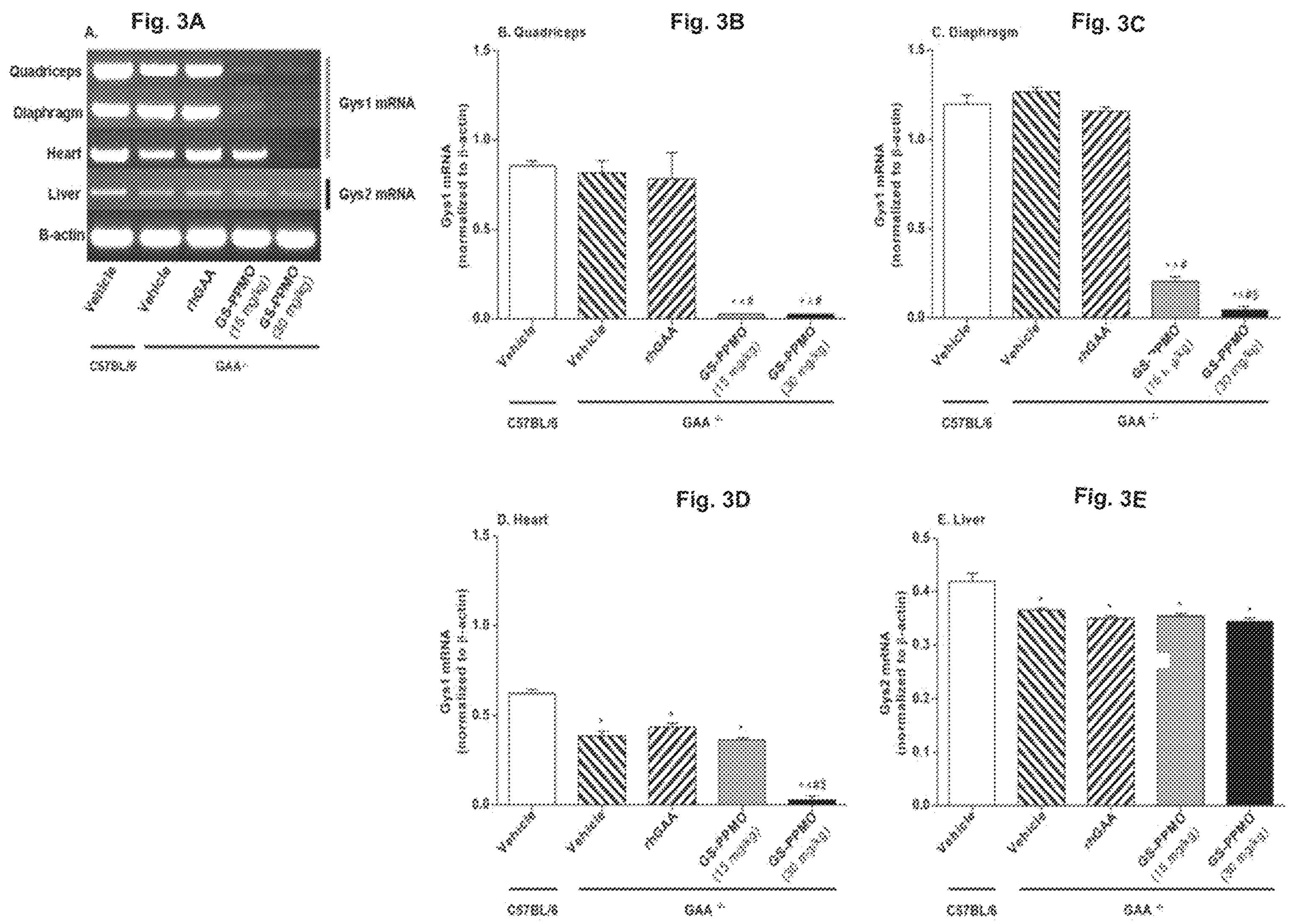

Gys1 protein levels are reduced in skeletal and cardiac muscles of Pompe mice treated with repeated intravenous injections of GS-PPMO Quadriceps
Diaphragm
Heart
Liver
gapdh
GYS1 protein
GYS1/2 protein
B. Quadriceps
C. Diaphragm
D. Heart
E. Liver
GYS1 protein (normalized to gapdh)
Vehicle
rhGAA
GS-PPMO (15 mg/kg)
GS-PPMO (30 mg/kg)
C57BL6
GAA -/-

Glycogen synthase activity is decreased in the quadriceps and heart muscles of Pompe mice treated with GS-PPMO Accumulation of lysosomal glycogen is abated in skeletal muscle of Pompe mice treated with GS-PPMO A. Quadriceps
Glycogen (mg/g of tissue)
Vehicle
Vehicle
rhGAA
GS-PPMO (15 mg/kg)
GS-PPMO (30 mg/kg)
C57BL/6
GAA -/-

B. Diaphragm

C. Heart

D. Liver

Fig. 7: Body weights of animals measured at the end of the study
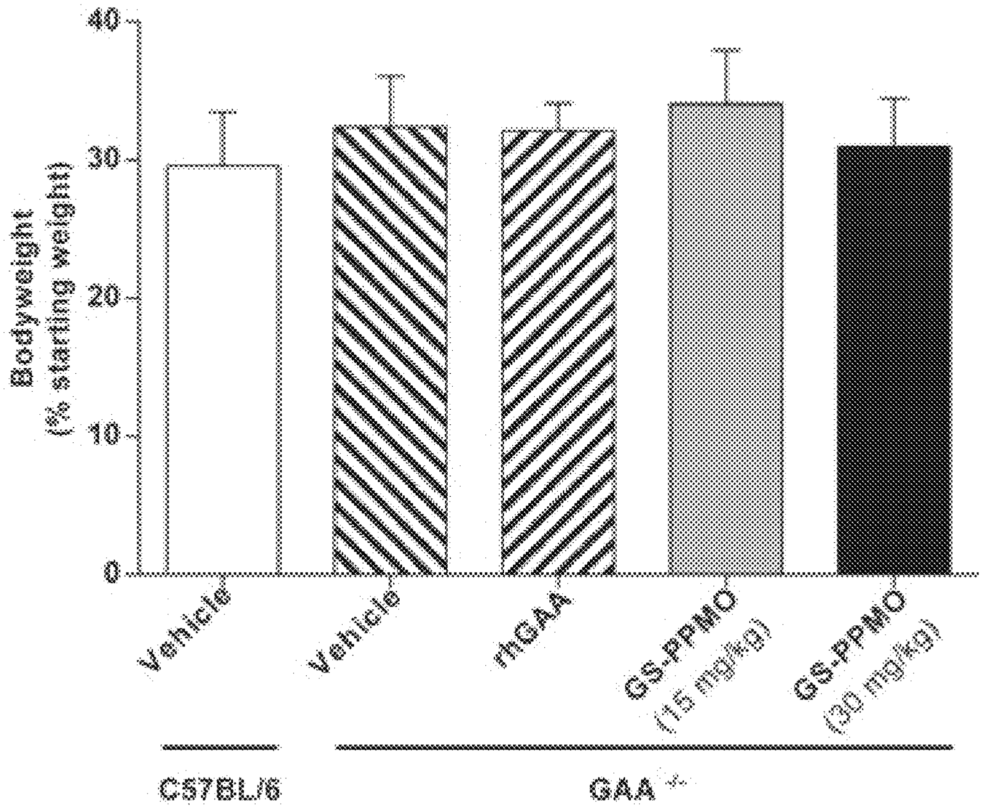

Serum chemistries of Pompe mice treated with GS-PPMO compared to control animals
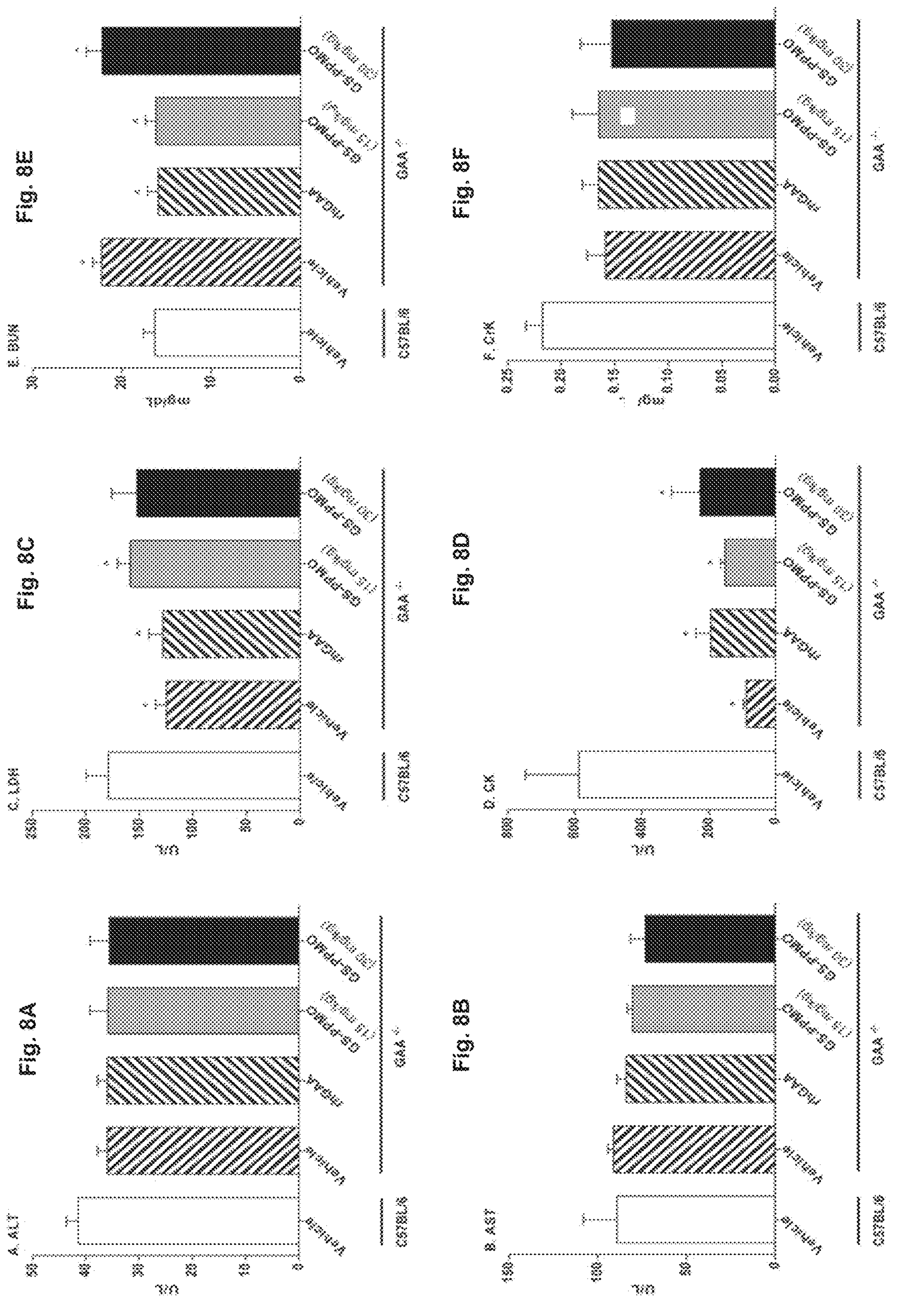

Histopathological analysis of kidney and liver of Pompe and wild type mice

Vehicle GS-PPMO (30mg/kg)

Vehicle GS-PPMO (30mg/kg)

INHIBITING OR DOWNREGULATING GLYCOGEN SYNTHASE BY CREATING PREMATURE STOP CODONS USING ANTISENSE OLIGONUCLEOTIDES

CROSS-REFERENCE TO RELATED APPLICATION

This application is a continuation of U.S. patent application Ser. No. 15/990,463, filed May 25, 2018, which is a continuation of U.S. patent application Ser. No. 15/313,387, which has the international filing date of May 22, 2015, which is a National Phase application under 35 U.S.C. § 371 of International Application No. PCT/US2015/032141, filed May 22, 2015, and claims the benefit of priority to U.S. Provisional Patent Application No. 62/002,294, filed May 23, 2014, the disclosures of which are incorporated herein by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 159792016402SEQLIST.TXT, date recorded: May 5, 2020, size: 78 KB).

DESCRIPTION OF THE INVENTION

Field of the Invention

The present disclosure relates to antisense oligonucleotides (AONs) for modulating the expression of glycogen synthase. AONs of the present disclosure may be useful in treating diseases associated with the modulation of the expression of the enzyme glycogen synthase, such as Pompe disease. Also provided by the present disclosure are compositions comprising AONs, as well as methods of down regulating mRNA coding for glycogen synthase, methods for reducing glycogen synthase in skeletal and cardiac muscle, and methods for treating Pompe disease.

SUMMARY OF THE INVENTION

Pompe disease is an inherited disorder caused by the accumulation of glycogen in the body's cells. This buildup of glycogen in the body, especially in skeletal and cardiac muscle, impacts the ability of the body's organs and tissues to function normally.

There are three known types of Pompe disease, including classic infantile-onset, non-classic infantile-onset, and late-onset. The classic form of infantile-onset begins within a few months of birth, and infants with this disorder experience myopathy, hypotonia, hepatomegaly, and heart defects, and death from heart failure typically results within the first year of life if not treated. Non-classic infantile-onset usually develops within the first year of life, and children with this disorder experience delayed motor skill development, progressive muscle weakness, and may have an enlarged heart. Serious breathing problems can occur and children with this form of Pompe disease do not live past early childhood. The last type of Pompe disease, late-onset, may not become apparent until much later in a person's life, including even into adulthood. Late-onset Pompe disease is usually milder than the infantile-onset forms and typically does not involve the heart. However, people with this form of the disease experience progressive muscle weakness, which can lead to breathing problems and may eventually lead to respiratory failure.

Pompe disease is caused by mutations in the GAA gene. The GAA gene encodes for acid alpha-glucosidase, which is an enzyme that breaks down glycogen into the simple sugar glucose. Mutations in the GAA gene lead to the genetic deletion of acid alpha-glucosidase. As a result, glycogen builds up in the cells and leads to the symptoms associated with Pompe disease.

Pompe disease is currently treated by enzyme replacement therapy using recombinant GAA. However, this method of treatment is not always entirely effective, and as a result, additional therapies for Pompe disease are needed.

Inhibiting the biosynthesis of glycogen is another potential means to treat patients with Pompe disease. So-called substrate reduction therapy is based on the inhibition of the main enzyme isoform responsible for building the glycogen polymer in skeletal muscle, glycogen synthase 1. Three methods have been reported that accomplish glycogen synthase 1 inhibition in Pompe mice: administration of a small interfering RNA (Douillard-Guilloux et al 2008); genetic knock down of the GSY1 gene in mice then crossed to Pompe mice (Douillard-Guiloux et at 2010); and inhibition of mTORC1 by administration of rapamycin (Ashe et at 2010). All three methods suppressed the accumulation of glycogen in Pompe mice. However, in the report by Ashe et at 2010 it was also reported that the administration of rapamycin and recombinant human GAA was significantly more effective at reducing glycogen accumulation in muscle tissue than either agent used alone. It was also revealed by Ashe et al that glycogen synthase enzyme activity is greatly elevated in Pompe mice suggesting that the absence of GAA and accumulation glycogen interferes with the normal regulation of the enzyme via phosphorylation. The dose of rapamycin needed to effect reduction of glycogen was the same as that required for immunosuppression indicating that it could not be used as a pharmacologic agent for the management of Pompe disease.

It is accordingly a primary object of the present disclosure to modulate the expression of glycogen synthase, resulting in beneficial effects for mammals who suffer from symptoms related to the buildup of glycogen in the body's cells.

Glycogen synthase is an enzyme involved in converting glucose into glycogen. In humans there are two different forms called isozymes or isoforms, glycogen synthase 1 and glycogen synthase 2, which are encoded for by the genes GYS1 and GYS2, respectively. Glycogen synthase 1 is expressed in muscles and other tissues, and glycogen synthase 2 is expressed only in the liver. GYS1 encodes for a pre-mRNA that has 16 exons. Exemplary human GYS1 sequences may be found at NCBI Reference Sequence: NM_002103.4 also shown in SEQ ID NO.: 1 (DNA/RNA) and SEQ ID NO.: 2 (CDS) or via the Human Gene Nomenclature Committee at HGNC: 4706 (see FIG. 1). Exemplary mouse GYS1 sequences may be found at NCBI Reference Sequence: NM030678.3 also shown in SEQ ID NO.: 3 (DNA/RNA) and SEQ ID NO.: 4 (CDS) or via the Human Gene Nomenclature Committee at MGI: 101805 (see FIG. 2).

According to the present disclosure, the modulation of pre-mRNA or mRNA transcribed from GYS1 may result in the down-regulation of glycogen synthase protein and reduce glycogen synthase enzyme activity in skeletal and cardiac muscle, as well as treat and/or prevent the symptoms associated with glycogen buildup in the muscles.

In one embodiment, the present disclosure relates to a method of down regulating mRNA coding for glycogen synthase comprising administering an effective amount of an antisense oligonucleotide to an animal, wherein the antisense oligonucleotide forms a sequence complementary to a nucleic acid sequence encoding for glycogen synthase, and wherein the hybridization of the antisense oligonucleotide to the nucleic acid sequence encoding for glycogen synthase Induces exon skipping. In one embodiment, the present disclosure relates to a method of down regulating mRNA coding for glycogen synthase comprising administering an effective amount of an antisense oligonucleotide to an animal, wherein the antisense oligonucleotide forms a sequence complementary to a nucleic acid sequence encoding for glycogen synthase, and wherein the hybridization of the antisense oligonucleotide to the nucleic acid sequence encoding for glycogen synthase induces translational inhibition. In one embodiment, the present disclosure relates to a method of down regulating mRNA coding for glycogen synthase comprising administering an effective amount of an antisense oligonudeotide to an animal, wherein the antisense oligonucleotide forms a sequence complementary to a nucleic acid sequence encoding for glycogen synthase, and wherein the hybridization of the antisense oligonucleotide to the nucleic acid sequence encoding for glycogen synthase induces suppression of polyadenylation.

One embodiment of the invention is method of down regulating mRNA coding for glycogen synthase comprising administering an effective amount of an antisense oligonucleotide to an animal, wherein the antisense oligonucleotide comprises a sequence complementary to a nucleic acid sequence encoding for glycogen synthase, and wherein the hybridization of the antisense oligonucleotide to the nucleic acid sequence encoding for glycogen synthase induces exon skipping. A further embodiment is of the invention is a method of down regulating mRNA coding for glycogen synthase comprising administering an effective amount of an antisense oligonucleotide to an animal, wherein the antisense oligonucleotide comprises a sequence complementary to a nucleic acid sequence encoding for glycogen synthase, and wherein the hybridization of the antisense oligonucleotide to the nucleic acid sequence encoding for glycogen synthase induces exon skipping, wherein the antisense oligonucleotide is a phosphorodiamidate morpholino oligo (also known as "PMO" or "morpholino") or wherein the antisense oligonucleotide is a PMO linked to a cell penetrating peptide ("CPP").

A further embodiment is of the invention is a method of down regulating mRNA coding for glycogen synthase comprising administering an effective amount of an antisense oligonucleotide to an animal, wherein the antisense oligonucleotide comprises a sequence complementary to a nucleic acid sequence encoding for glycogen synthase, and wherein the hybridization of the antisense oligonucleotide to the nucleic acid sequence encoding for glycogen synthase Induces exon skipping, wherein mRNA coding for glycogen synthase is reduced by up to 80%, up to 90% or up to 95%.

Additional objects and advantages of the present disclosure will be set forth in part in the description which follows, and in part will naturally flow from the description, or may be learned by practice of the disclosed embodiments. The objects and advantages of the present disclosure will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

FIGS. 1A and 1B: are the exemplary human GYS1 sequences as found at NCBI Reference Sequence: NM_002103.4 also shown in SEQ ID NO.: 1 (DNA/RNA) and SEQ ID NO.: 2 (CDS).

FIGS. 2A and 2B: are the exemplary mouse GYS1 sequences as found at NCBI Reference Sequence: NM_030678.3 also shown in SEQ ID NO.: 3 (DNA/RNA) and SEQ ID NO.: 4 (CDS).

FIGS. 3A-3E: Gys1 mRNA levels are reduced in skeletal and cardiac muscles of Pompe mice treated with repeated intravenous injections of GS-PPMO. (A) Semi-quantitative PCR analysis was performed on pooled samples of RNA prepared from tissues of wild type and Pompe mice that received the indicated treatments to determine Gys1 transcript levels. Gys1 mRNA levels (normalized to β-actin mRNA levels) were measured in the (B) quadriceps, (C) diaphragm, and (D) heart tissues. (E) Liver was examined for the impact of GS-PPMO on Gys2 mRNA levels. Data represent mean±SEM, n=4-5 mice per group. $P<0.05$, (*) compared to WT, (^) compared to vehicle, (#) compared to rhGAA, ($) compared to GS-PPMO at 15 mg/kg.

FIG. 7: Body weights of animals measured at the end of the study. Data is presented as mean±SEM, n=9-10 mice per group.

FIGS. 8A-8F: Serum chemistries of Pompe mice treated with GS-PPMO compared to control animals. (A-F) Levels of ALT, AST, LDH, CK, BUN, CrK (need to spell out all abbreviations) in serum collected 24 h after the final dose. Data represent mean±SEM, n=9-10 mice per group. P<0.05, (*) compared to WT, (^) compared to vehicle.

DEFINITIONS

Figures 4A, 4B, 4C, 4D, 4E:
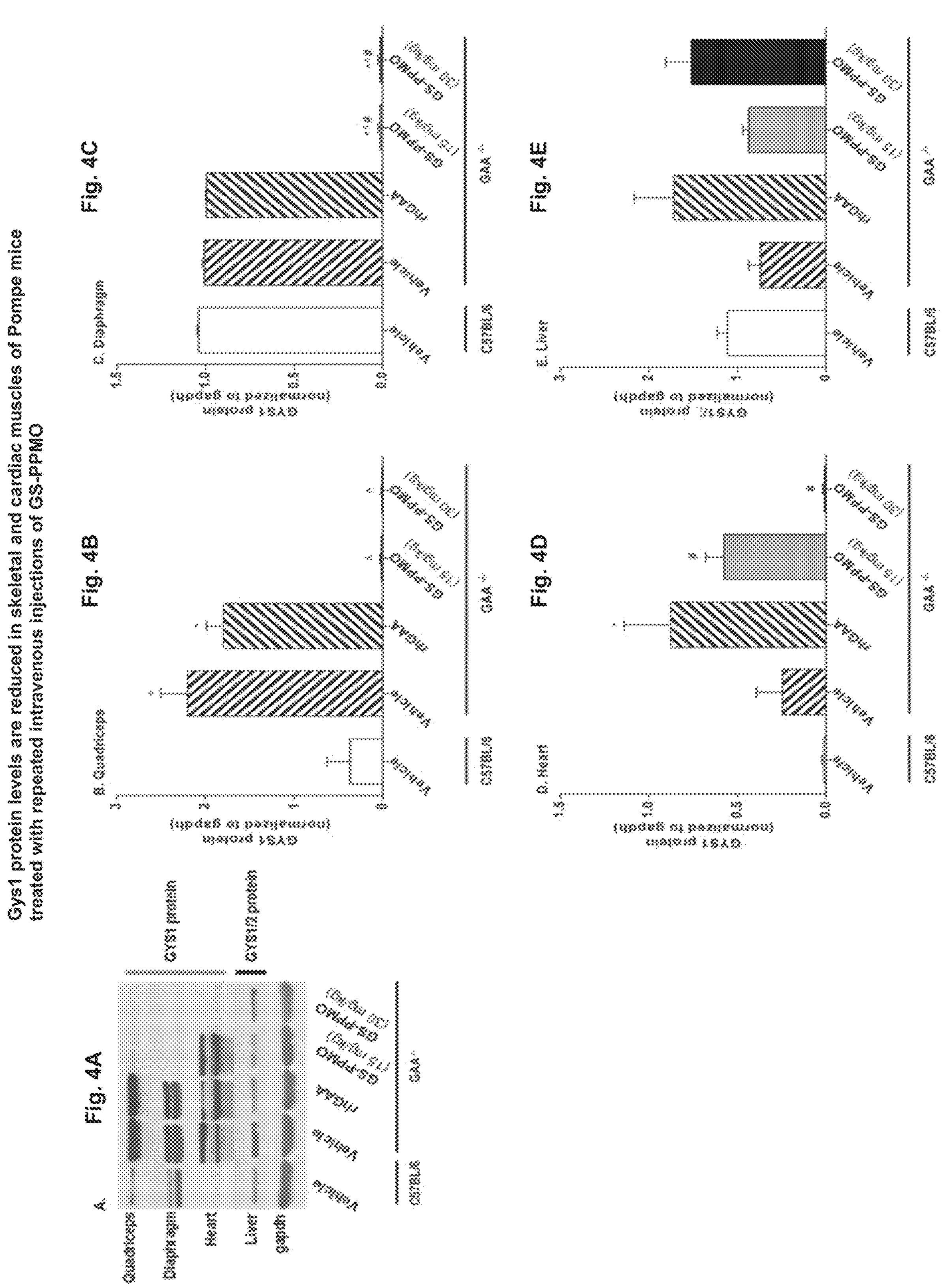
FIGS. 4A-4E: Gys1 protein levels are reduced in skeletal and cardiac muscles of Pompe mice treated with repeated intravenous injections of GS-PPMO. (A) Western blot analysis was carried out on pooled samples of protein lysates to assess GYS1 protein levels in tissues of wild type and Pompe mice that received the indicated treatments. GYS1 protein levels (normalized to gapdh protein levels), in the (B) quadriceps, (C) diaphragm, and (D) heart tissues were measured. (E) Liver was examined for the impact of GS-PPMO on Gys1/2 protein levels. Data represent mean±SEM, n=4-5 mice per group. $P<0.05$, (*) compared to WT, (^) compared to vehicle, (#) compared to rhGAA, ($) compared to GS-PPMO at 15 mg/kg.

Glycogen synthase is an enzyme involved in converting glucose into glycogen. In humans there are two different forms called isozymes or isoforms, glycogen synthase 1 and glycogen synthase 2, which are encoded for by the genes GYS1 and GYS2, respectively. Glycogen synthase 1 is located in muscles and other tissues, and glycogen synthase 2 is found only in the liver. GYS1 encodes for a pre-mRNA that has 16 exons. Exemplary human GYS1 sequences may be found at NCBI Reference Sequence: NM_002103.4 also shown in SEQ ID NO.: 1 (DNA/RNA) and SEQ ID NO.: 2 (CDS) or via the Human Gene Nomenclature Committee at HGNC: 4706 (see FIG. 1). Exemplary mouse GYS1 sequences may be found at NCBI Reference Sequence: NM_030678.3 also shown in SEQ ID NO.: 3 (DNA/RNA) and SEQ ID NO.: 4 (CDS) or via the Human Gene Nomenclature Committee at MGI: 101805 (see FIG. 2).

The term "RNA target" refers to an RNA transcript to which a morpholino binds in a sequence specific manner. In some embodiments the RNA target is one or more GSY1 mRNA or pre-mRNA molecules.

"Morpholino" or "morpholino antisense oligonucleotide" refer to an oligonucleotide analog composed of morpholino subunit structures, where (i) the structures are linked together by phosphorus-containing linkages, one to three atoms long, preferably two atoms long, and preferably uncharged or cationic, joining the morpholino nitrogen of one subunit to a 5' exocyclic carbon of an adjacent subunit, and (ii) each morpholino ring bears a purine or pyrimidine base-pairing moiety effective to bind, by base specific hydrogen bonding, to a base in a polynucleotide. In some embodiments, the morpholino binds to an RNA target which blocks translation of the RNA target into a protein. In other embodiments, the morpholino prevents aggregation of the RNA target with itself or with other cellular RNAs, proteins, or riboproteins, such as, but not limited to, RNAs, proteins, and riboproteins associated with the cellular mRNA splicing apparatus.

An "individual" can be a mammal, such as any common laboratory model organism, or any other mammal. Mammals include, but are not limited to, humans and non-human primates, farm animals, sport animals, pets, mice, rats, and other rodents.

As used herein. "treatment" (and grammatical variations thereof such as "treat" or "treating") refers to clinical intervention designed to alter the natural course of the individual or cell being treated during the course of clinical pathology. Desirable effects of treatment include, but are not limited to, decreasing the rate of disease progression, amelioration or palliation of the disease state, and remission or improved prognosis.

As used herein, "prevention" Includes providing prophylaxis with respect to occurrence or recurrence of a disease or the symptoms associated with a disease in an individual. An individual may be predisposed to, susceptible to, or at risk of developing a disease, but has not yet been diagnosed with the disease.

An "effective amount" or "therapeutically effective amount" refers to an amount of therapeutic compound, such as an antisense oligomer, administered to a mammalian subject, either as a single dose or as part of a series of doses, which is effective to produce a desired therapeutic effect. For an antisense oligomer, this effect is typically brought about by inhibiting translation or natural splice-processing of a selected target sequence.

As used herein, the singular form "a", "an", and "the" includes plural references unless indicated otherwise.

It is understood that aspects and embodiments of the invention described herein include "comprising," "consisting," and "consisting essentially of" aspects and embodiments.

It is intended that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

DETAILED DESCRIPTION OF THE INVENTION

Acid maltase or α-glucosidase (GAA) is a lysosomal enzyme that catalyzes the breakdown of glycogen to glucose. Mutations in the GAA gene that lead to a reduction in the amount or activity of the enzyme are the molecular basis of Pompe disease (glycogen storage disease type II). This autosomal recessive metabolic myopathy results as a consequence of the progressive accumulation of undegraded glycogen, primarily in the lysosomes of cardiac and skeletal muscle. Patients with Pompe disease (incidence of approximately 1 in 40,000) present with a broad spectrum of disease severity that is inversely correlated with the amount of residual enzyme activity. Complete loss of enzyme activity results in an Infantile presentation (so called "floppy babies") with affected individuals rarely living beyond 2 years of age. Varying degrees of residual enzyme activity lead to a progressive myopathy in young adults as well as older individuals that is invariably fatal.

Pompe disease is managed by periodic infusions of a recombinant enzyme (rhGAA) preparation that gained regulatory approval in 2006. Systemic infusion of rhGAA has been shown in clinical trials to improve cardiomyopathy and prolong survival in children and to improve walking ability as well as stabilize pulmonary function in adults. However, it is evident from long-term survivors that despite the availability of enzyme therapy, patients still present with some aspects of the disease. For example, residual muscle weakness and hearing loss are still evident, and the risk for developing arrhythmias, dysphagia and osteopenia remain undiminished. These residual deficits may be due in part to inefficient delivery of the enzyme to some of the affected tissues or to the host Immune response to the administered protein. In response to these unmet medical needs, modified forms of rhGAA conjugated with mannose 6-phosphate-bearing oligosaccharides or engineered to express a portion of IGF-1 have been developed that show improved delivery to muscle and bioactivity in animal studies. In addition, a small molecule chaperone that reportedly improves the stability of the enzyme and enhances glycogen clearance in Pompe mice is being tested clinically. Gene therapy with recombinant AAV vectors encoding the enzyme deficient in Pompe disease is also being evaluated as a treatment modality.

Substrate reduction that abates the production of glycogen represents yet another potential therapeutic strategy. The merits of this concept have been demonstrated in the context of the lysosomal storage disorders Gaucher and Fabry disease. Cytoplasmic glycogen polymers are synthesized through the action of glycogen synthase, whose activity is suppressed by phosphorylation of serines 641 and 645 in a process controlled by the mTORC1 pathway. Recent preclinical data have shown that glycogen synthase enzyme activity in Pompe mice is greatly elevated and that this increased activity could be suppressed by rapamycin treatment. Treating Pompe mice with rapamycin effectively reduced glycogen buildup in skeletal muscle, and when used in combination with rhGAA infusions lowered glycogen levels in skeletal muscle and diaphragm. Rapamycin treatment did not affect glycogen clearance in the heart, an organ already well served by rhGAA, perhaps due to the relatively high levels of the cation-independent mannose 6-phosphate receptors in cardiac tissue. An advantage of rapamycin as a substrate reduction approach was that Its impact on glycogen synthase was restricted to muscle, with no effect on the liver enzyme isoform. However, a disadvantage was that the lowest dose of rapamycin effective at reducing glycogen accumulation was also immunosuppressive.

The instant invention is directed to an alternative approach for reducing muscle glycogen levels in Pompe mice. Skeletal muscle glycogen synthase activity is the result of transcription of the Gys1 gene. In contrast, liver synthase activity is generated mostly by expression of the Gys2 gene and its encoded enzyme produces glycogen as a ready store of glucose for body-wide metabolism. Recent progress in developing therapies for Duchene muscular dystrophy has demonstrated that it is possible to deliver a therapeutically relevant dose of a phosphorodiamidate morpholino-based antisense oligonucleotide (PMO) for the purpose of skipping mutant exons and generating a truncated, albeit functional dystrophin. The PMO dose needed to restore dystrophin synthesis can be greatly reduced if it is conjugated to a cell penetrating peptide (PPMO). Delivery of a therapeutically relevant dose of a phosphorodiamidate morpholino-based antisense oligonucleotide (PMO) for the purpose of skipping mutant exons was utilized to induce exon skipping of the Gys1 mRNA for the purpose of reducing its transcript levels, presumably and without being limited as to theory, via nonsense mediated decay, with concomitant reductions in the skeletal muscle enzyme. Treating Pompe mice with a PPMO targeting a specific sequence in exon 6 of Gys1 mRNA (GS-PPMO) reduces in a dose dependent manner the Gys1 transcript in skeletal muscle and heart but not the Gys2 transcript in liver. Likewise, the glycogen synthase protein level is reduced in skeletal muscle and heart and synthase activity is restored. Consequently, glycogen accumulation is completely abated in skeletal muscle; the impact is less in the heart. These results Indicate that substrate reduction by antisense oligonucleotide (ASO)-mediated knock down of skeletal muscle glycogen synthase is a therapy, or an adjuvant therapy to enzyme replacement, for Pompe disease.

The present disclosure relates to oligomeric antisense compounds, i.e., AONs, such as phosphorodiamidate morpholino (PMO) compounds, peptide nucleic acids (PNAs). 2'-O alkyl (e.g., methyl) antisense oligonucleotides, and tricyclo-DNA antisense nucleotides for use in modulating pre-mRNA and mRNA transcribed from GYS1. The present disclosure also includes other AONs that result from other nucleotide modifications, such as for example, a modification to one or more of the non-bridging oxygens in the phosphodiester linkage. Such modifications lead to, for example, phosphorothioates. The present disclosure relates to any AON that specifically hybridize with one or more of pre-mRNA or mRNA transcribed from GYS1 and induce a reduction in glycogen accumulation in a disease state. The AONs contemplated for use in the instant invention include those attached to a cell-penetrating peptide (CPP) to enhance delivery. The AON-CPP may comprise multiple AON, including PMO AON, attached to a single CPP. In at least one embodiment of the present disclosure the multiple AON-CPP conjugate further comprises a cathepsin cleavable linker. The cathepsin cleavable linker can occur in between the AON and the CPP or it can occur in a sequence such as AON-cathepsin linker-AON-cathepsin linker-CPP. In another embodiment, the multiple PMO-CPP conjugate further comprises a cathepsin cleavable linker. The cathepsin cleavable linker can occur in between the PMO and the CPP or it can occur in a sequence such as PMO-cathepsin linker-PMO-cathepsin linker-CPP.

As used herein, an AON specifically hybridizes to a target polynucleotide, such as pre-mRNA or mRNA, when the AON hybridizes to the target under physiological conditions. In the context of the present disclosure, hybridization occurs via hydrogen bonding, which may be Watson-Crick, Hoogsteen or reversed Hoogsteen hydrogen bonding, between complementary purine and pyrimidine bases. For example, adenine (A) and thymine (T) are complementary nucleobases which pair through the formation of hydrogen bonds.

AONs, such as PMO compounds, of the present disclosure are complementary to a target pre-mRNA or mRNA when hybridization occurs according to generally accepted base-pairing rules. e.g., adenine (A)-thymine (T), cytosine (C)-guanine (G), adenine (A)-uracil (U). In particular, "complementary" as used herein refers to the capacity for precise pairing between two nucleobases. For example, if a base (B) at a certain position of an AON is capable of hydrogen binding with a nucleotide at the same position of a pre-mRNA or mRNA molecule, then the AON and the pre-mRNA or mRNA molecule are considered to be complementary to each other at that position. The AON and pre-mRNA or mRNA target are complementary to each other when a sufficient number of corresponding positions in each molecule are occupied by bases that can hydrogen bond with each other. Thus, "specifically hybridizable" and "complementary" are terms which are used to indicate a sufficient degree of complementarity or precise pairing such that stable and specific binding occurs between the AON, such as a PMO, and the pre-mRNA or mRNA target. Absolute complementarity, i.e., a 100% complementary base pair match, is not necessary as long as the heteroduplex formed between the target pre-mRNA or mRNA and the AON has sufficient stability to bring about the desired effect such as a reduction in glycogen accumulation.

According to the present disclosure, an AON, such as a PMO, is specifically hybridizable when binding of the AON to the target pre-mRNA or mRNA molecule Interferes with the normal function of the target pre-mRNA or mRNA molecule, and/or it brings about the desired effect, and there is a sufficient degree of complementarity to avoid intolerable non-specific binding of the AON to a non-target sequence under conditions in which specific binding is desired, for example under physiological conditions for in vivo applications or under conditions in which assays are performed for in vitro applications.

Such hybridization between an AON and pre-mRNA or mRNA interferes with their normal functions, such as translation of protein from the mRNA and splicing of the pre-mRNA to yield one or more mRNA species. In at least one embodiment of the present disclosure, the hybridization between the AON and pre-mRNA affects the splicing of the pre-mRNA to form stable RNA. In another embodiment the hybridization affects the translation of glycogen synthase 1 from mRNA.

AONs according to the present disclosure Include PMO compounds as well as PNA compounds, phosphoramidate compounds, methylene methylimino ("MMI") compounds, 2-O-methyl compounds and 2-methoxy ethyl compounds, wherein the oligonucleobase of each subunit are set forth in FIG. 1. The oligonucleotide compounds are synthetic analogs of natural nucleic acids. In particular, instead of deoxyribose rings and phosphate-linkages, the oligonucleotide compounds comprise subunits comprised of the respective oligonucleotide subunits shown below:

Formula I

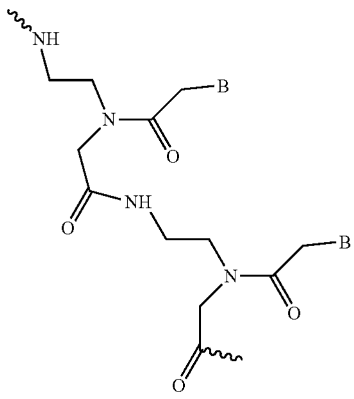

PNA

Formula II

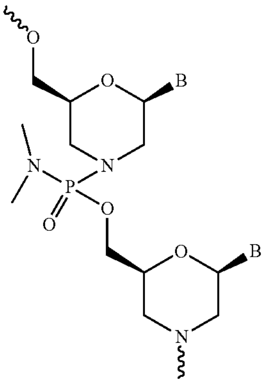

Morpholino

-continued

Formula III

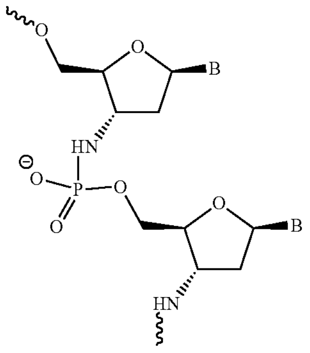

Phosphoramidate

Formula IV

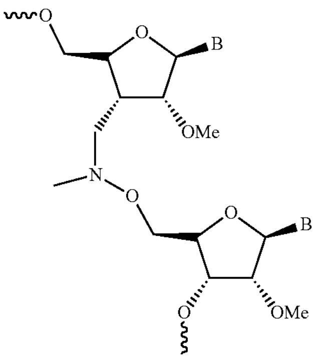

MMI

Formula V

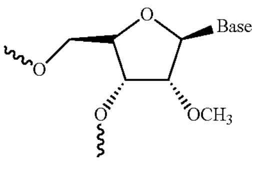

2-OMe

Formula VI

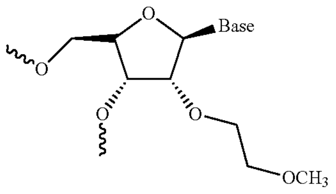

2-MOE

In the case of each of Formula 1-VI, B is a nucleotide base. The primary nucleobases are cytosine (DNA and RNA), guanine (DNA and RNA), adenine (DNA and RNA), thymine (DNA) and uracil (RNA), abbreviated as C, G, A. T. and U, respectively. A, G, C, and T appear in DNA, these molecules are called DNA-bases; A, G, C, and U are called RNA-bases. Uracil replaces thymine in RNA. These two bases are identical except that uracil lacks the 5' methyl group. Adenine and guanine belong to the double-ringed class of molecules called purines (abbreviated as R). Cytosine, thymine, and uracil are all pyrimidines (abbreviated as Y).

AON compositions can comprise morpholino oligonucleotide compositions. Morpholinos are synthetic molecules having a structure that closely resembles a naturally occurring nucleic acid. These nucleic acids bind to complementary RNA sequences by standard nucleic acid base pairing. Structurally, morpholinos differ from DNA or RNA in that these molecules have nucleic acid bases bound to morpholine rings instead of deoxyribose or ribose rings. Additionally, the backbone structure of morpholinos consists of non-ionic or cationic linkage groups instead of phosphates. For example, replacement of anionic phosphates with the uncharged phosphorodiamidate groups eliminates ionization in the usual physiological pH range, making morpholinos in organisms or cells uncharged molecules. Morpholinos are most commonly used as single-stranded oligos, though heteroduplexes of a morpholino strand and a complementary DNA strand may be used in combination with cationic cytosolic delivery reagents.

Unlike some other antisense structural types (e.g., phosphorothioates), morpholinos do not degrade their target RNA molecules. Instead, morpholinos act by "steric blocking," i.e., binding to a target sequence within an RNA and sterically hindering molecules which might otherwise interact with the RNA. Bound to the 5'-untranslated region of messenger RNA (mRNA), morpholinos can Interfere with progression of the ribosomal initiation complex from the 5' cap to the start codon. This prevents translation of the coding region of the targeted transcript (called "knocking down" gene expression). Some morpholinos knock down expression so effectively that after degradation of preexisting proteins the targeted proteins become undetectable by Western blot.

Morpholinos can also Interfere with pre-mRNA processing steps, usually by preventing splice-directing snRNP complexes from binding to their targets at the borders of introns on a strand of pre-RNA. Preventing U1 (at the donor site) or U2/U5 (at the polypyrimidine moiety and acceptor site) from binding can result in modified splicing, commonly leading to the exclusion of exons from a mature mRNA transcript. Splice modification can be conveniently assayed by reverse-transcriptase polymerase chain reaction (RT-PCR) and is seen as a band shift after gel electrophoresis of RT-PCR products.

Morpholinos have also been used to block intronic splice silencers and splice enhancers. U2 and U12 snRNP functions have been inhibited by morpholinos. Morpholinos targeted to "slippery" mRNA sequences within protein coding regions can induce translational frame shifts. Activities of morpholinos against this variety of targets suggest that morpholinos can be used as a general-purpose tool for blocking interactions of proteins or nucleic acids with mRNA.

In certain embodiments, the compositions of the present invention are composed of morpholino subunits linked together by uncharged phosphorus-containing linkages, one to three atoms long, joining the morpholino nitrogen of one subunit to the 5' exocyclic carbon of an adjacent subunit, wherein the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444, which is hereby incorporated by reference in its entirety. Variations can be made to this linkage as long as they do not interfere with binding or activity. For example, the oxygen attached to phosphorus may be substituted with sulfur (thiophosphorodiamidate). The 5' oxygen may be substituted with amino or lower alkyl substituted amino. The pendant nitrogen attached to phosphorus may be unsubstituted, monosubstituted, or disubstituted with (optionally substituted) lower alkyl. The purine or pyrimidine base pairing moiety is typically adenine, cytosine, guanine, uracil, thymine or inosine. The synthesis, structures, and binding characteristics of morpholinos are detailed in U.S. Pat. Nos. 5,698,685, 5,217,866, 5,142,047, 5,034,506, 5,166, 315, 5,521,063, 5,506,337, and International Patent Application Publication No. WO 2008/036127 all of which are incorporated herein by reference.

In some aspects, the morpholino antisense oligonucleotides of the present invention can be complementary to the pre mRNA sequences in the transcript emanating from the GSY1 locus. In some embodiments, the morpholino antisense oligonucleotide is at least any of about 90%, 95%, or 100%, inclusive, including any percentages in between these values, identical to an mRNA target. In another embodiment, the morpholino antisense oligonucleotide binds to the GSY1 mRNA transcript in a sequence-specific manner. In some embodiments, the morpholino antisense oligonucleotide comprises a 5' amine modification. In another embodiment, the morpholino antisense oligonucleotide can be a phosphorodiamidate cationic peptide-linked morpholino antisense oligonucleotide.

The morpholino antisense oligonucleotides described herein are linked to a cationic peptide which facilitates systemic delivery of the morpholino antisense oligonucleotides into muscle cells. In general, a cationic peptide as described herein can be 8 to 30 amino acid residues in length and consist of subsequences selected from the group consisting of RXR, RX, RB, and RBR: where R is arginine (which may include D-arginine), B is β-alanine, and each X is independently —NH—$(CHR^1)_n$—C(O)—, where n is 4-6 and each $R^1$ is independently H or methyl, such that at most two $R^1$'s are methyl. In some embodiments, each $R^1$ is hydrogen. In other embodiments, the cationic peptide can be any of 8, 9, 10, 11, 12, 13, 14, 15, 18, 17, 18, 19, 20, 21, 22, 23, 24, 25, 28, 27, 28, 29, or 30 amino acid residues in length. In another embodiment, the variable n is 5, e.g. as in 8-aminohexanoic acid. In one embodiment, the cationic peptide comprises the amino acid sequence $Ac(RXRRBR)_2XB$—, where Ac is an acetyl group. In another embodiment, the cationic peptide comprises the amino acid sequence $Ac(RXR)_4XB$—, where Ac is an acetyl group. Further information regarding synthesis and structure of cationic cell-penetrating peptides can be found in U.S. Patent Application Publication No. 2009/0099066, the disclosure of which is incorporated by reference herein in its entirety.

In one aspect, the cationic peptide is linked directly to the morpholino antisense oligonucleotide, in other embodiments, the cationic peptide is linked to the morpholino antisense oligonucleotide via a spacer moiety linked to the 5' end of the morpholino antisense oligonucleotide. The spacer moiety may be incorporated into the peptide during cationic peptide synthesis. For example, where a spacer contains a free amino group and a second functional group (e.g., a carboxyl group or an amino group) that enables binding to another molecular moiety, the spacer may be conjugated to a solid support used for peptide synthesis. Thereafter, the cationic peptide may be synthesized directly onto the spacer's free amino group by standard solid phase techniques. In some embodiments, the AON-CPP compound may comprise multiple AON, including PMO AON, attached to a single cationic peptide (CPP). In at least one embodiment of the present disclosure the multiple AON-CPP conjugate further comprises a cathepsin cleavable linker. The cathepsin cleavable linker can occur in between the AON and the CPP or It can occur in a sequence such as AON-cathepsin linker-AON-cathepsin linker-CPP. In another embodiment, the multiple PMO-CPP conjugate further comprises a cathepsin cleavable linker. The cathepsin cleavable linker can occur in between the PMO and the CPP or it can occur in a sequence such as PMO-cathepsin linker-PMO-cathepsin linker-CPP.

In another embodiment, the spacer moiety may be conjugated to the cationic peptide after peptide synthesis. Such conjugation may be achieved by methods well established in the art. In one embodiment, the linker contains at least one functional group suitable for attachment to the target functional group of the synthesized cationic peptide. For example, a spacer with a free amine group may be reacted with the cationic peptide's C-terminal carboxyl group. In some embodiments, the spacer moiety comprises:

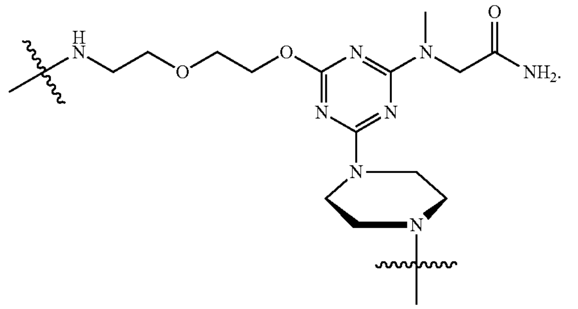

In one embodiment, the cationic peptide-linked morpholino antisense oligonucleotides have the following structure:

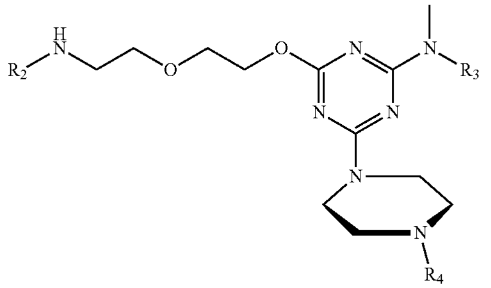

wherein $R^2$ is a cationic peptide (such as any of the cationic peptides disclosed herein), $R^3$ is H, $CH_3$ or $CH_2CONH_2$, and $R^4$ is a morpholino antisense oligonucleotide comprising the sequence 5'-$(AGC)_n$-3' (SEQ ID NO.: 5), 5'-$(GCA)_n$-3' (SEQ ID NO.: 6), or 5'-$(CAG)_n$-3' (SEQ ID NO.: 7), wherein n is any of about 5-25. In another embodiment, the cationic peptide-linked morpholino antisense oligonucleotides can further comprise 1 to 2 additional morpholino nucleotides on the 5' and/or 3' end of the oligonucleotides.

In another aspect, the cationic peptide linked morpholino antisense oligonucleotide comprises

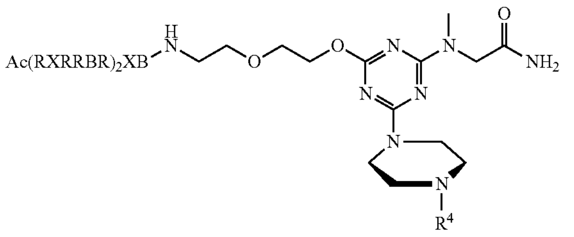

wherein Ac is acetyl, R is arginine (which may include D-arginine), B is β-alanine, each X is independently —NH—$(CHR^1)_n$—C(O)—, where n is 4-6 and each $R^1$ is H, and $R^4$ is a morpholino antisense oligonucleotide comprising a therapeutic sequence.

In another aspect, the cationic peptide linked morpholino antisense oligonucleotide comprises

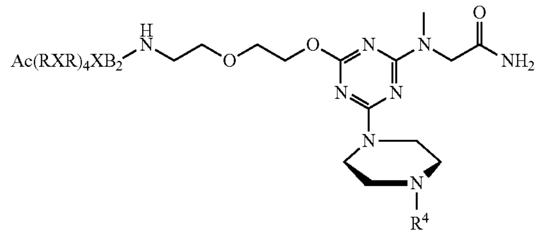

wherein Ac is acetyl, R is arginine (which may include D-arginine), B is β-alanine, each X is independently —NH— $(CHR^1)_n$—C(O)—, where n is 4-6 and each $R^1$ is H, and $R^4$ is a morpholino antisense oligonucleotide comprising a therapeutic sequence.

In some embodiments, compound may include a variable sequence—spacer—linker according to any of the sequences of Table 2 or Table 3; wherein R is L-arginine or arginine: X is 3-cis-aminocyclohexane or 1,3 cis-aminocyclohexane carboxylic acid; and Z Is cis-2-aminocyclopentane-1-carbonyl or cis-(1R,2S)-2-aminocyclopentane carboxylic acid. In some embodiments, X can be any combination of 0.1, or more residues that are R, X, and Z. In some embodiments, X can also include other types of residues, such as proline, glycine, or alanine, or additional modified or nonstandard amino acids. In some embodiments, the variable sequence includes alpha, beta, gamma, or delta amino acids, or cycloalkane structures. In some embodiments, the linker includes the sequence FS (SEQ ID NO.: 8). In some embodiments, the linker includes the sequence FSQ (SEQ ID NO.: 9) or FSQK (SEQ ID NO.: 10), wherein F is phenyalanine, S is serine, K is lysine and Q is glutamine. In some embodiments, the linker includes the sequence FxyB (SEQ ID NO.: 11), where x is any amino acid, standard or nonstandard, y is glutamic acid (E), aspartic acid (D), and lysine (K), serine (S), or threonine (T), and B is β-alanine or β-glycine.

TABLE 2

| Hit | Sequence | Localization | SEQ ID NO: |
|---|---|---|---|
| 2C4 | Ac-RXXXXXRRR(Ahx)FSQG-OH | Nucleus | 12 |
| 4G9 | Ac-RXXXXXXRR(Ahx)FSQG-OH | Nucleus | 13 |
| 9F5 | Ac-RXXXRXRXR(Ahx)FSQG-OH | Nucleus | 14 |
| 12G4 | Ac-RRXXZXXXR(Ahx)FSQG-OH | Nucleus | 15 |

TABLE 2-continued

| Hit | Sequence | Localization | SEQ ID NO: |
|---|---|---|---|
| 12D10 | Ac-RRRXXXXXR(Ahx)FSQG-OH | Nucleus | 16 |
| 12D11 | Ac-RXRXXXXXR(Ahx)FSQG-OH | Nucleus | 17 |
| 12E4 | Ac-RRZXXXXXR(Ahx)FSQG-OH | Nucleus | 18 |
| 21A5 | Ac-RXXXXZXZR(Ahx)FSQG-OH | Nucleus | 19 |
| 11G1 | Ac-RXXZXRXXR(Ahx)FSQG-OH | Cytosol | 20 |
| 12D4 | Ac-RRXRXXXXR(Ahx)FSQG-OH | Cytosol | 21 |
| 13D2 | Ac-RRZXXZXXR(Ahx)FSQG-OH | Cytosol | 22 |

In another embodiment, the cationic peptide linked to the morpholino antisense oligonucleotide is one of the peptides in Table 3.

TABLE 3

| Hit | Sequence | SEQ ID NO. |
|---|---|---|
| 9H8 | Ac-RXXXXXRXR(Ahx) | 23 |
| 9H9 | Ac-RZXXXXRXR(Ahx) | 24 |
| 9H11 | Ac-RXZXXXRXR(Ahx) | 25 |
| 1A2 | Ac-RRRRRRRRR(Ahx) | 26 |
| 12D12 | Ac-RZRXXXXXR(Ahx) | 27 |
| 13D3 | Ac-RXZXXZXXR(Ahx) | 28 |
| 12D10 | Ac-RRRXXXXXR(Ahx) | 29 |
| 2C4 | Ac-RXXXXXRRR(Ahx) | 30 |
| 4G9 | Ac-RXXXXXXRR(Ahx) | 31 |
| 11F4 | Ac-RXXXXRXXR(Ahx) | 32 |
| 9F5 | Ac-RXXXRXRXR(Ahx) | 33 |
| 12D11 | Ac-RXRXXXXXR(Ahx) | 34 |
| 20B7 | Ac-RXXXXXXZR(Ahx) | 35 |
| 20C4 | Ac-RXXZXXXZR(Ahx) | 36 |
| 5D4 | Ac-RXXXRZXRR(Ahx) | 37 |
| 9H7 | Ac-RRXXXXRXR(Ahx) | 38 |
| 5B1 | Ac-RXXXZXXRR(Ahx) | 39 |
| 4H6 | Ac-RXXZXXXRR(Ahx) | 40 |
| 12D4 | Ac-RRXRXXXXR(Ahx) | 41 |
| 15A8 | Ac-RXXXXXZXR(Ahx) | 42 |
| 12D8 | Ac-RXZRXXXXR(Ahx) | 43 |
| 12E3 | Ac-RZXXXXXXR(Ahx) | 44 |
| 12H2 | Ac-RXXZZXXXR(Ahx) | 45 |
| 4G10 | Ac-RZXXXXXRR(Ahx) | 46 |
| 15H5 | Ac-RXXXXZZXR(Ahx) | 47 |
| 11F1 | Ac-RXRXXRXXR(Ahx) | 48 |
| 21C7 | Ac-RRXXZZXZR(Ahx) | 49 |
| 12E2 | Ac-RXXXXXXXR(Ahx) | 50 |
| 12E4 | Ac-RRZXXXXXR(Ahx) | 51 |
| 12G4 | Ac-RRXXZXXXR(Ahx) | 52 |
| 21A5 | Ac-RXXXXZXZR(Ahx) | 53 |

When employed as pharmaceuticals, the antisense oligonucleotides, including cationic peptide-linked morpholino antisense oligonucleotides, disclosed herein can be formulated with a pharmaceutically acceptable excipient or carriers to be formulated into a pharmaceutical composition.

When employed as pharmaceuticals, the antisense oligonucleotides, including cationic peptide-linked morpholino antisense oligonucleotides, can be administered in the form of pharmaceutical compositions. These compounds can be administered by a variety of routes including oral, rectal, transdermal, subcutaneous, intravenous, intramuscular, and intranasal. These compounds are effective as both Injectable and oral compositions. Such compositions are prepared in a manner well known in the pharmaceutical art and comprise at least one active compound.

This invention also includes pharmaceutical compositions which contain, as the active ingredient, one or more of the antisense oligonucleotides, including cationic peptide-linked morpholino antisense oligonucleotides, associated with one or more pharmaceutically acceptable excipients or carriers. In making the compositions of this invention, the active ingredient is usually mixed with an excipient or carrier, diluted by an excipient or carrier or enclosed within such an excipient or carrier which can be in the form of a capsule, sachet, paper or other container. When the excipient or carrier serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients or carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 mg to about 100 mg or more, such as any of about 5 mg to about 10 mg, about 5 mg to about 20 mg, about 5 mg to about 30 mg, about 5 mg to about 40 mg, about 5 mg to about 50 mg, about 5 mg to about 60 mg, about 5 mg to about 70 mg, about 5 mg to about 80 mg, or about 5 mg to about 90 mg, inclusive, including any range in between these values, of the active ingredient. The term "unit dosage forms" refers to physically discrete units suitable as unitary dosages for individuals, each unit containing a predetermined quantity of active material calculated to produce the desired therapeutic effect, in association with a suitable pharmaceutical excipient or carrier.

The cationic peptide-linked morpholino antisense oligonucleotides are effective over a wide dosage range and are generally administered in a therapeutically effective amount. It will be understood, however, that the amount of the cationic peptide-linked morpholino antisense oligonucleotides actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient/cationic peptide-linked morpholino antisense oligonucleotide is mixed with a pharmaceutical excipient or carrier to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the letter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. The compositions can be administered by the oral or nasal respiratory route for local or systemic effect. Compositions in pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may also be administered, orally or nasally, from devices which deliver the formulation in an appropriate manner.

The overall effect of such interference with target pre-mRNA and mRNA transcribed from GYS1 is selective modulation of the expression of GYS1 and a change in glycogen accumulation. In the context of the present disclosure, "modulation" means either an increase (stimulation) or a decrease (inhibition) in the expression of a gene. According to the present disclosure, inhibition is the preferred form of modulation of gene expression. The modulation of the expression of GYS1 is selective over the modulation of GYS2 according to the present disclosure because the pre-mRNA and RNA transcribed from GYS1 is targeted rather than pre-mRNA and RNA transcribed from GYS2.

In at least one embodiment, the ASO compound has from 15-25 subunits of a subunit selected from Formulas (I)-(VI). In another embodiment, the ASO compound has from 20-25 subunits of a subunit selected from Formulas (I)-(VI). In yet another ASO, the ASO compound has about 25 subunits of a subunit selected from Formulas (I)-(VI), such as from 24-26 subunits.

In a specific embodiment, the ASO, including a PMO, has a nucleobase sequence of one of the sequences of Table 4: Identification of active phosphorodiamidate morpholino oligomer (PMO) sequences designed to target Gys1.

TABLE 4

| | Morpholino sequence | % Gys1 mRNA remaining | SEQ ID NO: |
|---|---|---|---|
| 1 | TCAGGGTTGTGGACTCAATCATGCC | 111 ± 14 | 54 |
| 2 | AAGGACCAGGGTAAGACTAGGGACT | 99.7 ± 0.1 | 55 |
| 3 | GTCCTGGACAAGGATTGCTGACCAT | 81 ± 16 | 56 |
| 4 | CTGCTTCCTTGTCTACATTGAACTG | 89 ± 7 | 57 |
| 5 | ATACCCGGCCCAGGTACTTCCAATC | 79 ± 10 | 58 |
| 6 | CTGGACAAGGATTGCTGACCATAGT | 72 ± 4 | 59 |
| 7 | AATTCATCCTCCCAGTCTTCCAATC | 71 ± 20 | 60 |
| 8 | TCCCACCGAGCAGGCCTTACTCTGA | 83 ± 21 | 61 |
| 9 | GACCACAGCTCAGACCCTACCTGGT | 8.7 ± 1.5 | 62 |
| 10 | TCACTGTCTGGCTCACATACCCATA | 7.8 ± 6.2 | 63 |

Gys1 mRNA levels were assessed in tibialis anterior muscles of C57Bl/6 mice injected with individual PMOs as described in the Materials and Methods. The PMO sequence (in line 10) targeting exon 6 for skipping and referred to herein as GS-PMO produced the greatest impact on Gys1 mRNA levels as assessed by semi-quantitative PCR and was selected for subsequent studies.

AONs, such as PMO compounds, according to the present disclosure that specifically hybridize to a target sequence at or near a splice site of pre-mRNA transcribed from GYS1 can lead to inclusion of an intron in the mRNA or to skipping both the intron and the exon near the splice site target. Either event can lead to the introduction of a premature stop codon, or a frame shift producing a nonsense mRNA. The inclusion of an exon usually leads to the inclusion of a stop codon in the reading frame of that intron. A frame shift caused by exon skipping also often leads to a premature stop codon in the frame-shifted exon. Premature stop codons are recognized and degraded by the nonsense-mediated machinery leading to exo and endo-nucleolytic mRNA degradation. (Bhuvanagiri et al., 2010) The degradation of mRNA transcribed from GYS1 may lead to down regulating mRNA coding for glycogen synthase 1, a reduced amount of glycogen synthase 1, and ultimately alleviation of symptoms associated with the buildup of glycogen in the cells.

Accordingly, the present disclosure includes a method of down regulating mRNA coding for glycogen synthase 1 comprising administering to an animal an AON, such as a PMO, according to the present disclosure.

The present disclosure also includes a method for reducing glycogen synthase 1 in skeletal and cardiac muscle comprising administering to an animal an AON, such as a PMO, according to the present disclosure.

Examples

Methods and Materials

Design of Phosphorodiamidate Morpholino Oligomers

Phosphorodiamidate morpholino oligomers (PMOs) were designed to hybridize to Gys1 mRNA so as to invoke either exon skipping or translation inhibition as described by Morcos. The sequences designed to skip exons in Gys1 mRNA are as follows:

(SEQ ID NO.: 54)
PMO 1 (5'-TCAGGGTTGTGGACTCAATCATGCC-3')

targeted the intronic sequence proximal to the splice acceptor site of intron 7;

(SEQ ID NO.: 55)
PMO 2 (5'-AAGGACCAGGGTAAGACTAGGGACT-3')

targeted the intronic sequence proximal to the splice acceptor site of intron 4;

(SEQ ID NO.: 56)
PMO 3 (5'-GTCCTGGACAAGGATTGCTGACCAT-3')

targeted the exon-intron boundary of exon 8;

(SEQ ID NO.: 57)
PMO 4 (5'-CTGCTTCCTTGTCTACATTGAACTG-3')

targeted the intron-exon boundary of exon 5;

(SEQ ID NO.: 58)
PMO 5 (5'-ATACCCGGCCCAGGTACTTCCAATC-3')

targeted the exon-intron boundary of exon 14;

(SEQ ID NO.: 59)
PMO 6 (5'-CTGGACAAGGATTGCTGACCATAGT-3')

similar to PMO 3 also targeted the exon-intron boundary of exon 8;

(SEQ ID NO.: 60)
PMO 7 (5'-AATTCATCCTCCCAGTCTTCCAATC-3')

was designed to inhibit translation initiation by targeting a sequence 3' to the initiation codon of Gys1;

(SEQ ID NO.: 61)
PMO 8 (5'-TCCCACCGAGCAGGCCTTACTCTGA-3')

targeted the exon-intron boundary of exon 7;

(SEQ ID NO.: 62)
PMO 9 (5'-GACCACAGCTCAGACCCTACCTGGT-3')

targeted the exon-intron boundary of exon 6.

(SEQ ID NO.: 63)
PMO 10 (5'-TCACTGTCTGGCTCACATACCCATA-3')

targeted the exon-intron boundary of exon 5;

Conjugation of Cell-Penetrating Peptides to Morpholino Oligonucleotides

PPMO conjugation was conducted as previously described by Abes et al. J Control Release. Dec. 1, 2006; 116(3):304-313 with modifications. Peptide B (Ac (RXRRBR)2XB—OH) (SEQ ID NO.: 64) was activated in dimethylformamide containing O-(6-Chlorobenzotriazol-1-yl)-N,N,N,N'-tetramethyluronium hexafluorophosphate (HCTU)diisopropylethylamine (DIEA) at molar ratios of 1:2 per moles of peptide at room temperature (RT). The Morpholino, GS1-ES6, (5'-TCACTGTCTGGCTCACATACCCATA-3') (SEQ ID NO.: 63) with a 5' primary amine modification was dissolved in dimethylsulfoxide and added to activated peptide at a 1.2-1.5:1 molar ratio of peptide: ASO and allowed to react at RT for 2 h; when completed the reaction was quenched with water. PPMO conjugates were separated from unbound PMO by isolation over carboxymethyl sepharose and eluted in 2M guanidine-HCl, 1M NaCl, pH 7.5, 20% acetonitrile. The eluate was dialyzed against several buffer exchanges of 0.1 mM $NaHCO_3$ in a dialysis cassette with molecular weight cut-off of 3,000 Da. The dialyzed PPMO was quantified by spectrophotometric absorbance in 0.1N HCl at 265 nm, frozen, and lyophilized. Molecular weight of conjugated GS1-ES6 PPMO was confirmed by MALDI mass spectrometry.

In-Vivo Experiments

Animal experiments were conducted in accordance with the Guide for the Care and Use of Laboratory Animals (US Department of Health and Human Services, NIH Publication No. 86-23) and by Genzyme's IACUC committee.

Intramuscular TA Injections

Six week-old C57BL/6 mice were anesthetized with isoflurane and the tibialis anterior (TA) muscle was injected as previously described [Wheeler T M et al., J Clin Invest. December 2007; 117(12):3952-3957]. TA muscles were injected with 12 uL of 0.4 U/μL bovine hyaluronidase 2 hours before PMO injection and electroporation. One TA was injected with 20 μg (1 μg/μl) of various PMOs (Table 4) and the contralateral TA with 20 μl phosphate buffered saline (PBS). Immediately following injection, the muscle was electroporated using the parameters of 100 V/cm, 10 pulses at 1 Hz, and 20 ms duration per pulse. Mice were euthanized two weeks after electroporation and TA muscle collected and snap frozen until analysis.

Systemic Administration

Six week-old male and female $GAA^{-/-}$ and C57BL/6 mice were employed to evaluate the efficacy of substrate inhibition using peptide-linked morpholinos. Tissues were collected from a cohort of animals at the start of the studies to serve as a baseline reference for the glycogen accumulation assay (n=10). GS-PPMO was dissolved in PBS and administered at 15 or 30 mg/kg bodyweight by tail vein injection once every 2 weeks for a total of 12 weeks (n=9-10). The positive control, rhGAA, was reconstituted in a buffer consisting of 25 mM sodium phosphate pH 6.2, 2% mannitol, and 0.005% polysorbate 80 and 20 mg/kg administered by tail vein injection once every 2 weeks for 12 weeks (buffer, n=10; rhGAA, n=10). To minimize the potential for a hypersensitivity reaction to rhGAA, mice were intraperitoneally pretreated with 5 mg/kg diphenhydramine starting at the third dose of rhGAA. Two weeks after the final dose mice were euthanized, tissues collected and snap frozen in liquid nitrogen for in vitro analyses or fixed in 10% neutral buffered formalin for histological analysis.

In-Vitro Experiments

RNA Analysis

Total RNA was isolated from frozen tissue using a commercially available kit with optional DNA digestion. RT-PCR was conducted using custom primers used for cDNA synthesis and PCR amplification. Primer sequences: Gys1 forward, 5'-CTGGCGCTGTGGACTTCTA-3' (SEQ ID NO.: 65), Gys1 reverse, 5-ACACTGGTGGGAAAGACTGC-3' (SEQ ID NO.: 66). Gys2 forward, 5'-CCAGCTTGACAAGTTCGACA-3 (SEQ ID NO.: 67), Gys2 reverse, 5'-AAACACCCCAAGGTGACAAC-3' (SEQ ID NO.: 68), b-actin forward, 5'-AGCCATGTACGTAGCCATCC-3' (SEQ ID NO.: 69) and b-actin reverse, 5'-CTCTCAGCTGTGGTGGTGAA-3' (SEQ ID NO.: 70). RT-PCR products (25 cycles) were separated on 2% agarose gels containing ethidium bromide and scanned on a bio-imaging system. Band intensity was quantified using Image J software. Levels of Gys1 and Gys2 mRNA was determined relative to beta actin.

Preparation of Tissue Homogenates

Tubes containing frozen tissues with 6× (vol/wt) homogenization buffer designed to inhibit phosphatases and proteases (20 mM Tris/HCL, pH 7.5, 150 mM NaCl, 25 mM B-glycerophosphate, 20 mM Sodium Fluoride, 1 mM Sodium Orthovanadate, 2 mM Sodium Pyrophosphate, 2 mM EDTA and complete protease inhibitor cocktail were homogenized. Lysates were frozen for 24 hours at −80 C. Thawed lysates were centrifuged 16.1 rcf for 15 minutes at 4 C; the supernatants were aliquoted and stored at −80 C. Protein determination of the lysates was performed with a Micro BCA kit.

Western Blot Analysis of Tissue Lysate 50-100 μg of tissue homogenate was boiled in 2× sample buffer containing dithiothreitol. The lysate was then applied to a 4-15% precast Tris/HCl-polyacrylamide gel. Proteins were transferred to nitrocellulose with a dry blot apparatus. The blots were blocked overnight with 3% milk and the appropriate antibody added at a final concentration of 0.02-0.08 ng/ml and incubated for 1 hr at room temp. The blot was then incubated with an HRP-conjugated secondary antibody for 1 hr at room temperature and treated with an ECL substrate detection kit as described by the manufacturer. Protein band intensity was quantified using Image J software. Levels of glycogen synthase 1 and 2 protein was determined relative to GAPDH.

Glycogen Synthase Activity Assay

Glycogen synthase activity in tissue lysates was measured using a gel filtration radioactivity assay as described previously [Niederwanger A et al., J of Chromatography B, 2005:820:143-145]. A 60 μL reaction solution consisting of 10 μg of protein lysate (2 ng/μL), 4% glycogen, 30 mM UDP-glucose, 4.5 mM glucose-6-phosphate, homogenization buffer (described above) and labeled uridine diphosphate glucose [Glucose-$^{14}$C-U] was incubated in a 37° C. water bath for 1 h, the reaction was stopped with 0.6N perchloric acid, and 50 μL of the reaction was loaded onto a quick spin (G-50) sephadex columns and centrifuged at 1000×g for 4 min. The eluted radiation was added to LSC cocktail and radiation was measured using a scintillation counter. Enzyme activity was calculated by determining the amount of UDP-[U—$^{14}$C]-glucose incorporated into glycogen per minute per milligram of protein Measurement of Tissue Glycogen Tissue glycogen levels were determined as previously described (Ziegler R J et al., Hum Gene Ther. June 2008; 19(6):609-211. Fluorescence was detected and analyzed using a micro-plate reader, 530 nm excitation and 590 nm emission, with acquisition and analysis software. Rabbit liver glycogen was used to construct the standard curve. Glycogen levels were determined by subtracting the glucose levels in the undigested samples from those in the digested samples.

Serum Chemistry

Whole blood was collected in serum separator tubes from the retro-orbital plexus of anesthetized mice one hour after the final dose of GS-PPMO. Blood was allowed to clot for thirty minutes and then centrifuged at 1300×g for fifteen minutes. Serum was dispensed as aliquots and frozen at −20° C. until analysis. In-vitro diagnostic quantitative determination of chemistry analytes in serum was performed by spectrophotometric methods at 37° C.

Histology

Kidney and liver were collected from mice following euthanasia, fixed for up to 72 h in 10% neutral buffered formalin and processed for paraffin embedding. Serial 5 μm-thick sections were generated and stained with hematoxylin and eosin solution. A board certified veterinary pathologist, blinded-to the treatments, evaluated the slides for qualitative analysis.

Statistical Analysis

Data is expressed as mean t SEM. Data analysis was performed using one way ANOVA and Newman-Keuls post-hoc. A probability value of $P<0.05$ was considered to be statistically significant.

PMO-based antisense oligonucleotide confers selective knockdown of Gys1 mRNA in murine muscle.

A collection of PMO antisense oligonucleotides was designed to selectively reduce the expression of the Isoform of glycogen synthase found mainly in skeletal muscle and heart with the potential to induce exon skipping in the cognate Gys1 but not the Gys2 transcript. Exon skipping was designed to introduce a premature stop codon into the Gys1 transcript to effect the production of an unstable mRNA prone to nonsense-mediated decay. Incorporation of a nonsense codon would also be expected, after translation, to lead to a non-functional enzyme.

Candidate ASOs were first tested by direct Injection into the TA muscle of mice followed by electroporation. One week later Gys1 mRNA levels were quantified. Twelve ASOs were tested and two resulted in what appeared to be a substantial reduction in Gys1 mRNA (Table 4). One PMO sequence in particular (number 10 in Table 4) targeted the skipping of exon 6 and was evaluated further.

The selected PMO was synthesized with a 5' primary amine to facilitate conjugation of a well-characterized arginine-rich cell penetrating sequence that had been shown previously to facilitate muscle delivery. This conjugated PMO (GS-PPMO) was injected through a tail vein into Pompe mice once every two weeks for a total of 12 weeks. Age-matched Pompe mice administered saline vehicle or 20 mg/kg recombinant α-glucosidase (rhGAA) on the same schedule served as treatment controls. Age-matched wild type (C57Bl/6) mice served as untreated controls. Analysis of tissue extracts from Pompe mice at the end of the study showed that treatment with either 15 or 30 mg/kg GS-PPMO significantly reduced Gys1 mRNA levels in the quadriceps and diaphragm muscle (FIGS. 3A, 3B and 3C). Gys1 mRNA levels were also dramatically reduced in the heart, but only after treatment with the higher dose (FIG. 30). No significant changes were seen in the steady state levels of Gys2 mRNA in the liver, indicating that GS-PPMO-mediated knockdown was specific for the muscle isoform of glycogen synthase (FIG. 3E). As expected, treating animals with rhGAA had no impact on Gys1 mRNA levels in skeletal muscle or heart or the Gys2 mRNA levels in liver.

Systemic administration of GS-PPMO to Pompe mice selectively reduces glycogen synthase 1 levels.

Western blots were used to assess the degree to which the reductions in Gys1 mRNA led to concomitant reductions in glycogen synthase protein in muscle and liver. In Pompe mice, glycogen synthase protein was found to be substantially elevated in the skeletal muscle and in the heart compared to C57I/6 control animals (FIG. 4A-E). This increase was not due to higher levels of mRNA (FIG. 3) and may therefore be related to an increase in the stability of the enzyme in these Pompe tissues. However, there were no differences in the levels of glycogen synthase in the liver of Pompe mice compared to those of wild type control animals.

Treatment of Pompe mice with GS-PPMO (15 or 30 mg/kg) lowered the amount of glycogen synthase in the quadriceps and diaphragm to wild type levels (FIGS. 4A, 4B and 4C). Treatment also reduced the elevated levels of glycogen synthase in the Pompe mouse heart, and achieved complete correction at the higher (30 mg/kg) dose (FIG. 4D). Neither dose of GS-PPMO affected the amount of total glycogen synthase in the liver (FIG. 4E). Treating Pompe mice with rhGAA also did not significantly alter the amount of glycogen synthase in the tissues tested.

Systemic administration of GS-PPMO reduces glycogen synthase activity in the skeletal muscle and heart of Pompe mice.

Figure 5A:
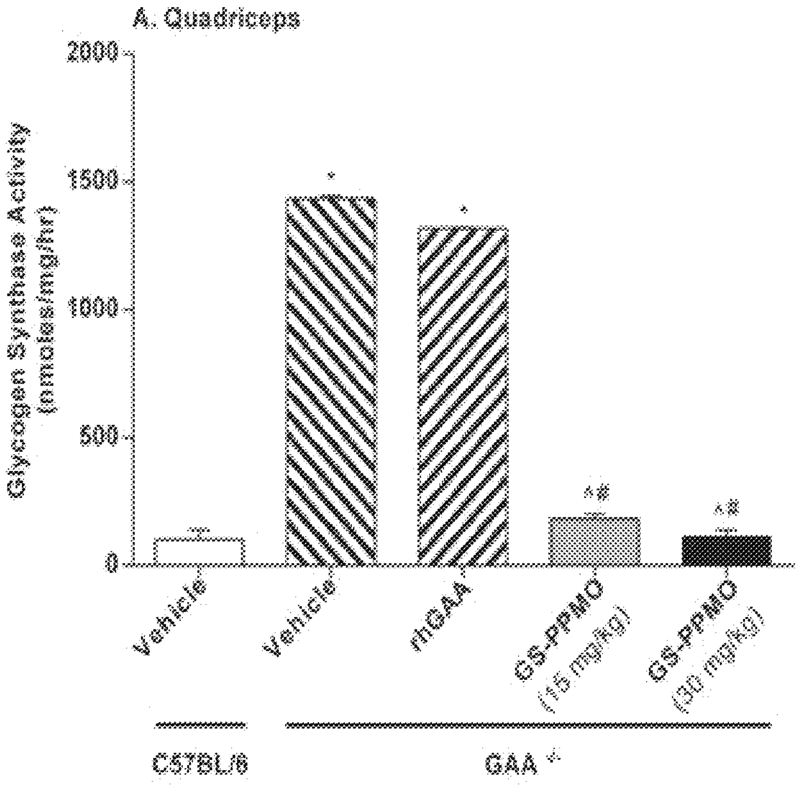
FIGS. 5A and 5B: Glycogen synthase activity is decreased in the quadriceps and heart muscles of Pompe mice treated with GS-PPMO. Glycogen synthase activity in the (A) quadriceps and (B) heart of wild type and Pompe mice was assayed as described in the Materials and Methods. Data represent mean±SEM, n=4-5 mice per group. $P<0.05$, (*) compared to WT, (^) compared to vehicle, (#) compared to rhGAA, ($) compared to GS-PPMO at 15 mg/kg.
Figure 5B:
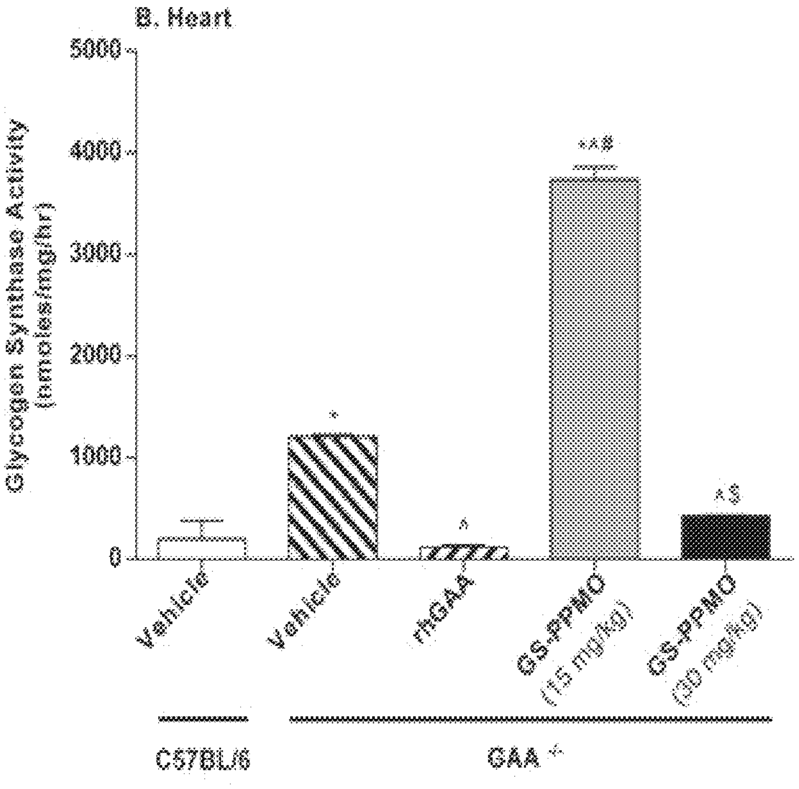

Treating Pompe mice with GS-PPMO led to complete correction of the elevated glycogen synthase activity in the quadriceps (FIG. 5A). A reduction of enzyme activity in the heart was observed only in Pompe mice treated at the higher dose of 30 mg/kg GS-PPMO (FIG. 58) whereas an apparent increase in activity was noted at the lower dose. In general, these findings are consistent with the mRNA and protein measurements noted above. Treating Pompe mice with rhGAA (at the dose tested) had no effect on glycogen synthase activity in the skeletal muscle but lowered that in the heart to normal levels. This differential response to treatment with the recombinant enzyme is consistent with previous reports in Pompe mice.

Systemic treatment with GS-PPMO abates accumulation of tissue glycogen in Pompe mice.

Figures 6A, 6B, 6C, 6D:
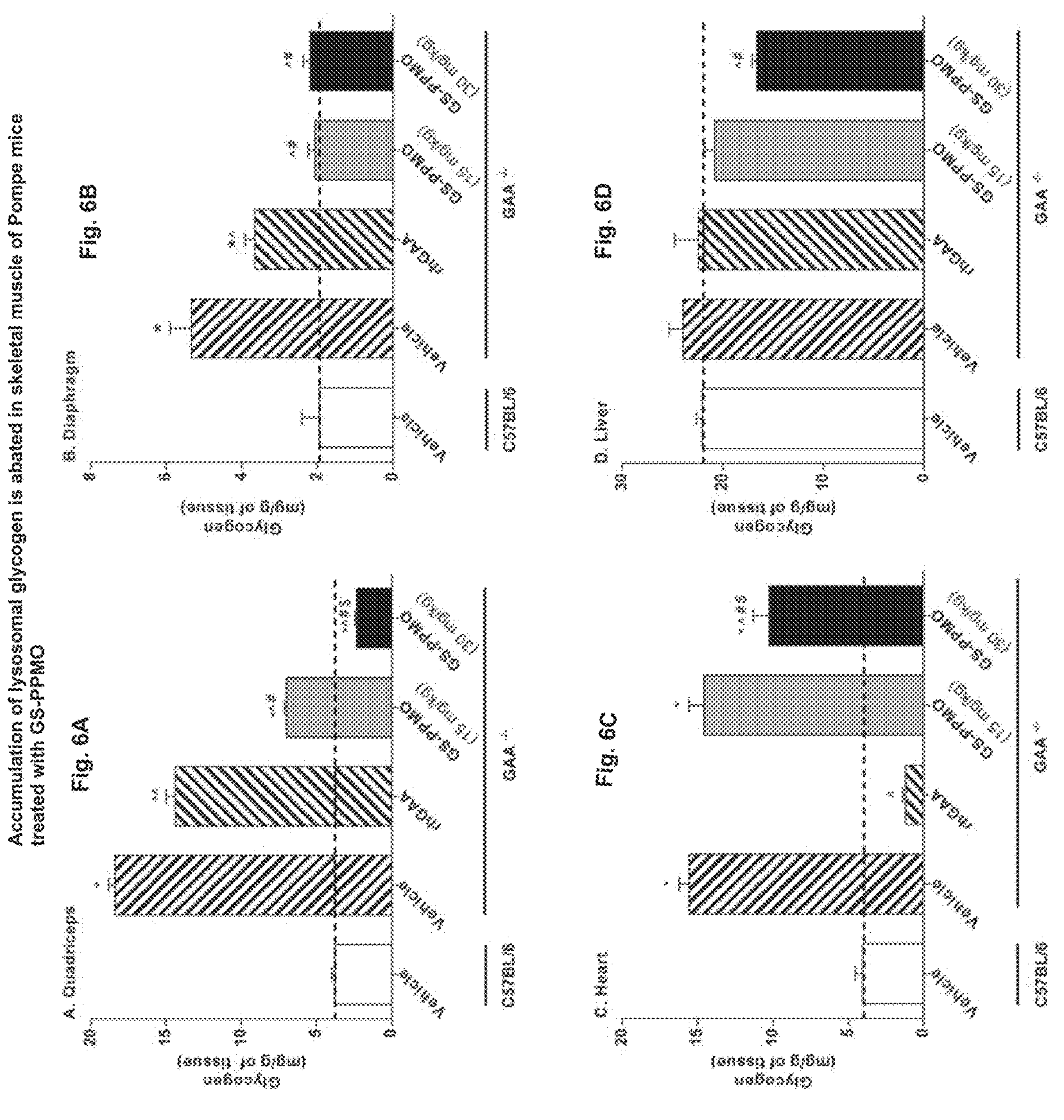
FIGS. 6A-6D: Accumulation of lysosomal glycogen is abated in skeletal muscle of Pompe mice treated with GS-PPMO. Glycogen levels in the (A) quadriceps, (B) diaphragm, (C) heart and (D) liver of Pompe and wild type mice were measured using the amplex red assay described in the Materials and Methods. Data represent mean SEM, n=4-5 mice per group. $P<0.05$, (*) compared to WT, (^) compared to vehicle, (#) compared to rhGAA, ($) compared to GS-PPMO at 15 mg/kg.

Tissue extracts were subjected to quantitative glycogen analysis to determine whether the noted reductions in glycogen synthase protein levels and activity in GS-PPMO-treated Pompe mice also resulted in a concomitant lowering of lysosomal glycogen accumulation. Treating Pompe mice with GS-PPMO led to a dose dependent decrease in glycogen accumulation in the quadriceps and heart (FIGS. 6A and 6C), and a reduction to the level found in normal control mice in the diaphragm at both doses tested (FIG. 6B). In the quadriceps and diaphragm of Pompe mice treated with 30 mg/kg GS-PPMO, the levels of glycogen were reduced to those found in wild type C57Bl/6 mice. As expected, Pompe mice treated with 20 mg/kg rhGAA showed a partial reduction in glycogen levels in the quadriceps, diaphragm and a greater reduction in the heart (FIG. 6). Neither treatment with rhGAA nor GS-PPMO (15 mg/kg) had an impact on glycogen levels in the liver. However, treatment with the higher dose (30 mg/kg) of GS-PPMO did result in a partial reduction in liver glycogen levels (FIG. 60).

Systemic administration of GS-PPMO does not elicit overt changes in histopathology and blood chemistry.

Figure 9A:
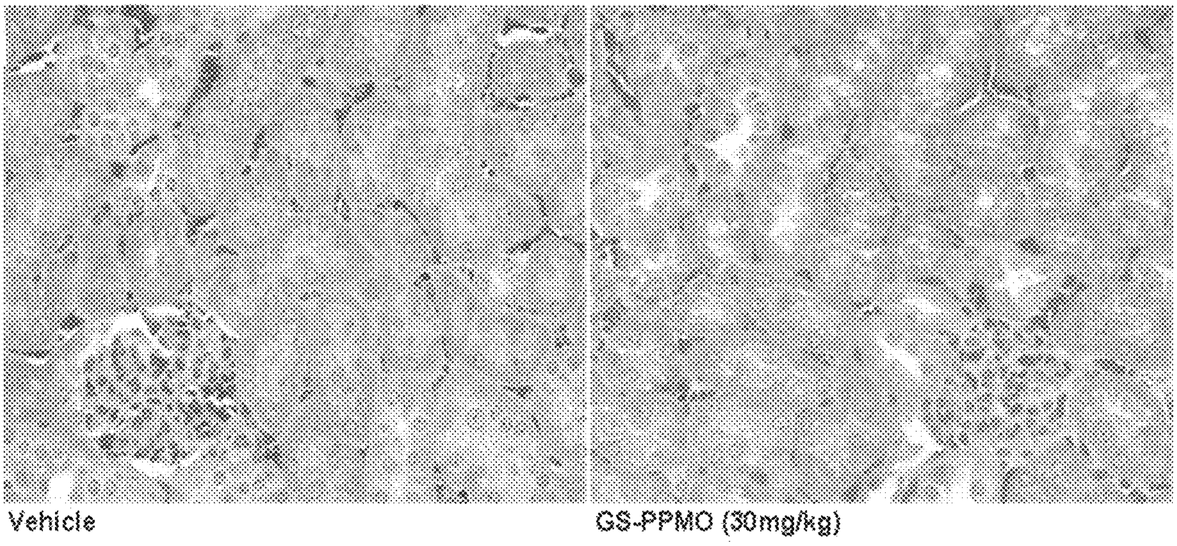
FIGS. 9A and 9B: Histopathological analysis of kidney and liver of Pompe and wild type mice. Hematoxylin and eosin stained slides were prepared from mice treated with either vehicle of GS-PPMO as indicated. (A) Kidney sections of GS-PPMO treated Pompe mice show a normal architecture of proximal convoluted tubules and glomeruli. (B) Livers of GS-PPMO-treated Pompe mice exhibit the presence of Kupffer cells in hepatocytes. Magnification=40× .
Figure 9B:
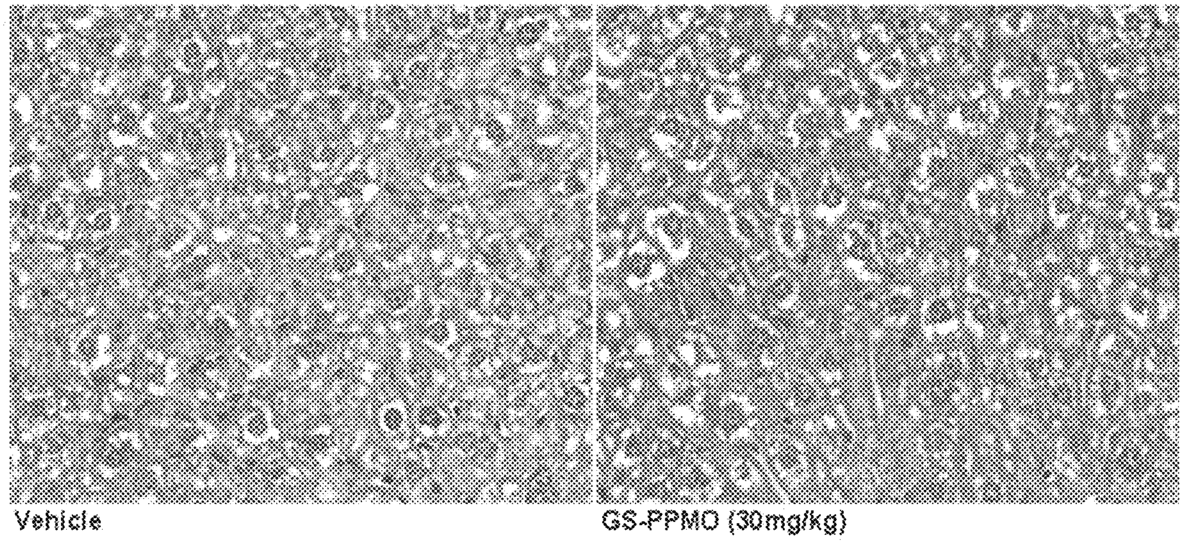

The potential toxicologic impact of GS-PPMO treatment and knockdown of GYS1 mRNA was evaluated to assess the therapeutic index associated with administering a PMO-based ASO for Pompe disease. Pompe mice treated with either dose of GS-PPMO did not demonstrate significant differences in weight gain from mice in the control cohort (FIG. 7). Examination of blood biomarkers of liver, muscle and kidney damage also did not reveal any deviations from those noted in control mice (FIG. 8). Finally, histological analysis of the kidney and liver of GS-PPMO-treated Pompe mice revealed normal architecture and the absence of discernible lesions (FIG. 9). These data suggests that systemic administration of GS-PPMO is well tolerated, at the doses tested.

GS-PPMO was capable of provoking Gys1 mRNA decreases in quadriceps, diaphragm and heart in a dose dependent manner. The bioactivity seen in the heart was only significant at the higher dose tested, a finding consistent with PPMOs tested for exon skipping of dystrophin (data not shown). GS-PPMO activity at the mRNA level appeared to be sequence specific as there was no impact on the liver isoform, Gys2. This finding was expected given that GS-PPMO is complementary to intron sequence in Gys1. The fact that GS-PPMO appears specific for the muscle enzyme suggests that its action will not interfere with systemic glucose mobilization in Pompe patients, which is governed by the predominant liver enzyme encoded by the Gys2 gene. Also as expected, administration of rhGAA had no impact on the steady state level of Gys1 or Gys2 mRNA in any tissue tested.

The GS-PPMO mediated knock down of Gys1 mRNA greatly reduced the amount of Gys1 protein in quadriceps and diaphragm at both doses tested, and also in the heart at the higher dose. These findings are impressive given the elevation of the protein in these tissues seen in Pompe mice compared to control animals. There was no change in the level of liver Gys2 protein which is consistent with the designed specificity of GS-PPMO towards Gys1 mRNA. The effect of GS-PPMO treatment on glycogen synthase enzyme activity in the quadriceps and heart was further evaluated and substantial reduction was found in both tissues as well as some noteworthy differences. Glycogen synthase activity was considerably elevated in the quadriceps and heart of Pompe mice; a finding consistent with the protein levels cited above and previous reports. Treating Pompe mice with GS-PPMO reduced activity in these tissues to very near the wild type levels found in C57Bl/6 mice at both doses tested. This was also true in the heart but only with the higher dose employed. It is remarkable to note that even with the elevated level of GS-activity in the untreated Pompe heart, the administration of GS-PPMO (15 mg/kg) increased GS-activity further by 200-fold. Glycogen synthase activity is regulated at the level of protein phosphorylation that is controlled by environmental conditions through the mTOR pathway.

The effect of rhGAA and GS-PPMO treatment on glycogen build up in Pompe mice was also assessed. Analysis of quadriceps and diaphragm after treatment with rhGAA at 20 mg/kg both revealed modest declines in glycogen compared to vehicle-treated Pompe mice. Treatment with GS-PPMO was significantly more effective at abating glycogen build up in the quadriceps and diaphragm, the latter tissue being equally amenable to treatment with either dose. The heart showed complete abatement of glycogen build up by rhGAA treatment to a level even below that found in untreated C57Bl/6 control mice. This is in contrast to the aforementioned increase in GS activity and may be due to the well-noted presence of CI-M6P receptors in the heart permitting greater efficacy of rhGAA in that tissue. GS-PPMO treatment resulted in a modest dose-dependent decline of glycogen build up in heart.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of down regulating mRNA coding for glycogen synthase comprising administering an effective amount of an antisense oligonucleotide to an animal, wherein the antisense oligonucleotide comprises SEQ ID NO:58, 59, or 60, and wherein the hybridization of the antisense oligonucleotide to the nucleic acid sequence encoding for glycogen synthase induces exon skipping.

2. The method of claim 1, wherein the antisense oligonucleotide is a phosphorodiamidate morpholino oligo (PMO).

3. The method of claim 1, wherein the antisense oligonucleotide is a PMO linked to a cell penetrating peptide (CPP).

4. The method of claim 1, wherein the antisense oligonucleotide is selected from an oligonucleotide comprising subunits of one of Formula I-VI:

(I)

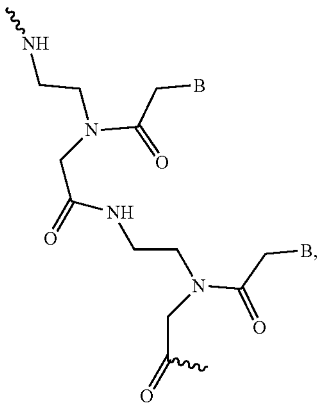

(II)

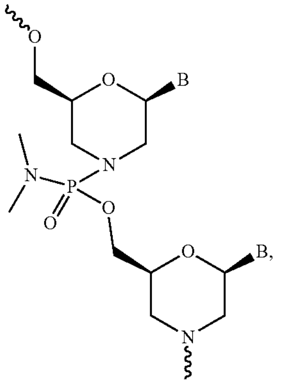

(III)

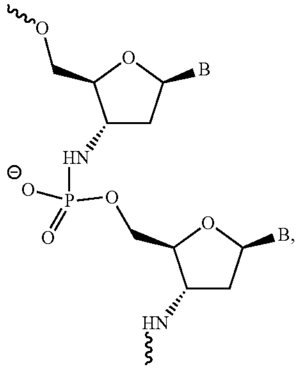

-continued (IV)

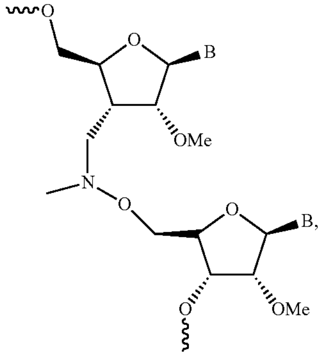

(V)

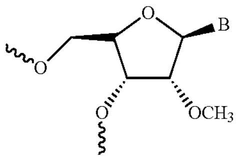

or (VI)

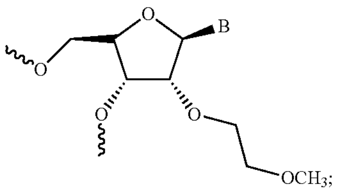

wherein B in each of Formula I-VI is a nucleotide base.

5. The method of claim 1, wherein the effective amount ranges from 5 to 500 mg per dose.

6. The method of claim 1, wherein the compound is administered intravenously.

7. The method of claim 1, wherein the down regulation of mRNA coding for glycogen synthase occurs in skeletal and cardiac muscle.

8. A method for reducing glycogen synthase in skeletal and cardiac muscle comprising administering to an animal an effective amount of an antisense oligonucleotide, wherein the antisense oligonucleotide comprises a sequence selected from the group consisting of SEQ ID NO:58, 59, and 60, and wherein the hybridization of the antisense oligonucleotide to the nucleic acid sequence encoding for glycogen synthase induces exon skipping.

9. A method for treating Pompe disease comprising administering to an animal an effective amount of an antisense oligonucleotide, wherein the antisense oligonucleotide comprises a sequence selected from the group consisting of SEQ ID NOs:58, 59, and 60, and wherein the hybridization of the antisense oligonucleotide to the nucleic acid sequence encoding for glycogen synthase induces exon skipping.

10. The method of claim 1, wherein the antisense oligonucleotide comprises SEQ ID NO:58.

11. The method of claim 1, wherein the antisense oligonucleotide comprises SEQ ID NO:59.

12. The method of claim 1, wherein the antisense oligonucleotide comprises SEQ ID NO:60.

13. The method of claim 8, wherein the antisense oligonucleotide comprises SEQ ID NO:58.

14. The method of claim 8, wherein the antisense oligonucleotide comprises SEQ ID NO:59.

15. The method of claim 8, wherein the antisense oligonucleotide comprises SEQ ID NO:60.

16. The method of claim 9, wherein the antisense oligonucleotide comprises SEQ ID NO:58.

17. The method of claim 9, wherein the antisense oligonucleotide comprises SEQ ID NO:59.

18. The method of claim 9, wherein the antisense oligonucleotide comprises SEQ ID NO:60.

* * * * *

UNITED STATES PATENT AND TRADEMARK OFFICE

CERTIFICATE OF CORRECTION

PATENT NO. : 11,801,311 B2
APPLICATION NO. : 16/867261
DATED : October 31, 2023
INVENTOR(S) : Nelson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 251 days.

Signed and Sealed this
First Day of July, 2025

Coke Morgan Stewart
*Acting Director of the United States Patent and Trademark Office*

SEQUENCE LISTING

<160> NUMBER OF SEQ ID NOS: 71

<210> SEQ ID NO 1
<211> LENGTH: 3635
<212> TYPE: DNA
<213> ORGANISM: Homo sapiens

<400> SEQUENCE: 1
tcctggcggc tgcgaggttt cactgcaggg gcgccagtgg gctcagtgac gctgcggcct 60
ccttctgcct aggtcccaac gcttcggggc aggggtgcgg tcttgcaata ggaagccgag 120
cgtcttgcaa gcttcccgtc gggcaccagc tactcggccc cgcaccctac ctggtgcatt 180
ccctagacac ctccggggtc cctacctgga gatccccgga gcccccccttc ctgcgccagc 240 catgccttta aaccgcactt tgtccatgtc ctcactgcca ggactggagg actgggagga 300
tgaattcgac ctggagaacg cagtgctctt cgaagtggcc tgggaggtgg ctaacaaggt 360
gggtggcatc tacacggtgc tgcagacgaa ggcgaaggtg acaggggacg aatggggcga 420
caactacttc ctggtggggc cgtacacgga gcagggcgtg aggacccagg tggaactgct 480
ggaggccccc accccggccc tgaagaggac actggattcc atgaacagca agggctgcaa 540
ggtgtatttc gggcgctggc tgatcgaggg aggccctctg gtggtgctcc tggacgtggg 600
tgcctcagct tgggccctgg agcgctggaa gggagagctc tgggatacct gcaacatcgg 660
agtgccgtgg tacgaccgcg aggccaacga cgctgtcctc tttggctttc tgaccacctg 720
gttcctgggt gagttcctgg cacagagtga ggagaagcca catgtggttg ctcacttcca 780
tgagtggttg gcaggcgttg gactctgcct gtgtcgtgcc cggcgactgc ctgtagcaac 840
catcttcacc acccatgcca cgctgctggg gcgctacctg tgtgccggtg ccgtggactt 900
ctacaacaac ctggagaact tcaacgtgga caaggaagca ggggagaggc agatctacca 960
ccgatactgc atggaaaggg cggcagccca ctgcgctcac gtcttcacta ctgtgtccca 1020
gatcaccgcc atcgaggcac agcacttgct caagaggaaa ccagatattg tgacccccaa 1080
tgggctgaat gtgaagaagt ttctgccat gcatgagttc cagaacctcc atgctcagag 1140
caaggctcga atccaggagt ttgtgcgggg ccatttttat gggcatctgg acttcaactt 1200
ggacaagacc ttatacttct ttatcgccgg ccgctatgag ttctccaaca agggtgctga 1260
cgtcttcctg gaggcattgg ctcggctcaa ctatctgctc agagtgaacg gcagcgagca 1320
gacagtggtt gccttcttca tcatgccagc gcggaccaac aatttcaacg tggaaaccct 1380
caaaggccaa gctgtgcgca aacagctttg ggacacggcc aacacggtga aggaaaagtt 1440
cgggaggaag ctttatgaat ccttactggt tgggagcctt cccgacatga acaagatgct 1500
ggataaggaa gacttcacta tgatgaagag agccatcttt gcaacgcagc ggcagtcttt 1560 ccccccctgtg tgcacccaca atatgctgga tgactcctca gaccccatcc tgaccaccat 1620
ccgccgaatc ggcctcttca atagcagtgc cgacagggtg aaggtgattt tccacccgga 1680
gttcctctcc tccacaagcc ccctgctccc tgtggactat gaggagtttg tccgtggctg 1740
tcaccttgga gtcttcccct cctactatga gccttggggc tacacaccgg ctgagtgcac 1800
ggttatggga atccccagta tctccaccaa tctctccggc ttcggctgct tcatggagga 1860
acacatcgca gacccctcag cttacggtat ctacattctt gaccggcggt tccgcagcct 1920
ggatgattcc tgctcgcagc tcacctcctt cctctacagt ttctgtcagc agagccggcg 1980
gcagcgtatc atccagcgga accgcacgga gcgcctctcc gaccttctgg actggaaata 2040
cctaggccgg tactatatgt ctgcgcgcca catggcgctg tccaaggcct ttccagagca 2100

-continued

```
cttcacctac gagcccaacg aggcggatgc ggcccagggg taccgctacc cacggccagc   2160

ctcggtgcca ccgtcgccct cgctgtcacg acactccagc ccgcaccaga gtgaggacga   2220

ggaggatccc cggaacgggc cgctggagga agacggcgag cgctacgatg aggacgagga   2280

ggccgccaag gaccggcgca acatccgtgc accagagtgg ccgcgccgag cgtcctgcac   2340

ctcctccacc agcggcagca agcgcaactc tgtggacacg gccacctcca gctcactcag   2400

caccccgagc gagcccctca gccccaccag ctccctgggc gaggagcgta actaagtccg   2460

ccccaccaca ctccccgcct gtcctgcctc tctgctccag agagaggatg cagaggggtg   2520

ctgctcctaa acccccgctc cagatctgca ctgggtgtgg ccccgcagtg cccccaccca   2580

gtccgccaaa cactccaccc cctccagctc cagtttccaa gttcctgcac tccagaatcc   2640

acaaagccgt gcctttctct ggctccagaa tatgcataat cagcgccctg gagtcccctg   2700

ggcctggacc gcttcccaga ggccaggaat ctgccattac tctgcggtgg tgccagaggt   2760

tttaggaaac ctggcatggt gctttcaggt ctggggcttt tagagccccc cgtgtggctt   2820

acaaattcta cagcatacag agcaggccac gctcaggccc ggcatgcggg ccaccaagtt   2880

ctggaaacca cgtggtgtcc ctgcgaatgg ggcgatcaag tccagagccg gggcactttc   2940

agagtttgaa ggtaactgag agcagatggt cctccatttc aactccagaa gtggggctct   3000

gggagggatg ttctagccct ccctggcatg tcagagccag gctctgcctg gaggatccct   3060

ccatccggct cctgtcatcc cctacacttt ggccaagcaa gaggtggtag aaccacttgg   3120

ctgctcattc cttctggagg acacacagtc tcagtccaga tgccttcctg tctttctggc   3180

cctttctgga ccagatccta ctcttccttt ctaaatctga gatctccctc cagggaatcc   3240

gcctgcagag gacagagctg gctgtcttcc cccaccccta acctggctta ttcccaactg   3300

ctctgcccac tgtgaaacca ctaggttcta ggtcctggct tctagatctg gaaccttacc   3360

acgttactgc atactgatcc ctttcccatg atccagaact gaggtcactg ggttctagaa   3420

cccccacatt tacctcgagg ctcttccatc cccaaactgt gccctgcctt cagctttggt   3480

gaaagggagg gcccctcatg tgtgctgtgc tgtgtctgca ccgcttggtt tgcagttgag   3540

aggggagggc aggaggggtg tgattggagt gtgtccggag atgagatgaa aaaaatacat   3600

ctatatttaa gaatcccaaa aaaaaaaaaa aaaaa                             3635
```

<210> SEQ ID NO 2
<211> LENGTH: 737
<212> TYPE: PRT
<213> ORGANISM: Homo sapiens

<400> SEQUENCE: 2

```
Met Pro Leu Asn Arg Thr Leu Ser Met Ser Ser Leu Pro Gly Leu Glu
1               5                   10                  15

Asp Trp Glu Asp Glu Phe Asp Leu Glu Asn Ala Val Leu Phe Glu Val
            20                  25                  30

Ala Trp Glu Val Ala Asn Lys Val Gly Gly Ile Tyr Thr Val Leu Gln
        35                  40                  45

Thr Lys Ala Lys Val Thr Gly Asp Glu Trp Gly Asp Asn Tyr Phe Leu
    50                  55                  60

Val Gly Pro Tyr Thr Glu Gln Gly Val Arg Thr Gln Val Glu Leu Leu
65                  70                  75                  80

Glu Ala Pro Thr Pro Ala Leu Lys Arg Thr Leu Asp Ser Met Asn Ser
                85                  90                  95
```

-continued

```
Lys Gly Cys Lys Val Tyr Phe Gly Arg Trp Leu Ile Glu Gly Gly Pro
            100                 105                 110

Leu Val Val Leu Leu Asp Val Gly Ala Ser Ala Trp Ala Leu Glu Arg
        115                 120                 125

Trp Lys Gly Glu Leu Trp Asp Thr Cys Asn Ile Gly Val Pro Trp Tyr
    130                 135                 140

Asp Arg Glu Ala Asn Asp Ala Val Leu Phe Gly Phe Leu Thr Thr Trp
145                 150                 155                 160

Phe Leu Gly Glu Phe Leu Ala Gln Ser Glu Glu Lys Pro His Val Val
                165                 170                 175

Ala His Phe His Glu Trp Leu Ala Gly Val Gly Leu Cys Leu Cys Arg
            180                 185                 190

Ala Arg Arg Leu Pro Val Ala Thr Ile Phe Thr Thr His Ala Thr Leu
        195                 200                 205

Leu Gly Arg Tyr Leu Cys Ala Gly Ala Val Asp Phe Tyr Asn Asn Leu
    210                 215                 220

Glu Asn Phe Asn Val Asp Lys Glu Ala Gly Glu Arg Gln Ile Tyr His
225                 230                 235                 240

Arg Tyr Cys Met Glu Arg Ala Ala Ala His Cys Ala His Val Phe Thr
                245                 250                 255

Thr Val Ser Gln Ile Thr Ala Ile Glu Ala Gln His Leu Leu Lys Arg
            260                 265                 270

Lys Pro Asp Ile Val Thr Pro Asn Gly Leu Asn Val Lys Lys Phe Ser
        275                 280                 285

Ala Met His Glu Phe Gln Asn Leu His Ala Gln Ser Lys Ala Arg Ile
    290                 295                 300

Gln Glu Phe Val Arg Gly His Phe Tyr Gly His Leu Asp Phe Asn Leu
305                 310                 315                 320

Asp Lys Thr Leu Tyr Phe Phe Ile Ala Gly Arg Tyr Glu Phe Ser Asn
                325                 330                 335

Lys Gly Ala Asp Val Phe Leu Glu Ala Leu Ala Arg Leu Asn Tyr Leu
            340                 345                 350

Leu Arg Val Asn Gly Ser Glu Gln Thr Val Val Ala Phe Phe Ile Met
        355                 360                 365

Pro Ala Arg Thr Asn Asn Phe Asn Val Glu Thr Leu Lys Gly Gln Ala
    370                 375                 380

Val Arg Lys Gln Leu Trp Asp Thr Ala Asn Thr Val Lys Glu Lys Phe
385                 390                 395                 400

Gly Arg Lys Leu Tyr Glu Ser Leu Leu Val Gly Ser Leu Pro Asp Met
                405                 410                 415

Asn Lys Met Leu Asp Lys Glu Asp Phe Thr Met Met Lys Arg Ala Ile
            420                 425                 430

Phe Ala Thr Gln Arg Gln Ser Phe Pro Pro Val Cys Thr His Asn Met
        435                 440                 445

Leu Asp Asp Ser Ser Asp Pro Ile Leu Thr Thr Ile Arg Arg Ile Gly
    450                 455                 460

Leu Phe Asn Ser Ser Ala Asp Arg Val Lys Val Ile Phe His Pro Glu
465                 470                 475                 480

Phe Leu Ser Ser Thr Ser Pro Leu Leu Pro Val Asp Tyr Glu Glu Phe
                485                 490                 495

Val Arg Gly Cys His Leu Gly Val Phe Pro Ser Tyr Tyr Glu Pro Trp
            500                 505                 510

Gly Tyr Thr Pro Ala Glu Cys Thr Val Met Gly Ile Pro Ser Ile Ser
```

-continued

```
        515                 520                 525

Thr Asn Leu Ser Gly Phe Gly Cys Phe Met Glu Glu His Ile Ala Asp
    530                 535                 540

Pro Ser Ala Tyr Gly Ile Tyr Ile Leu Asp Arg Arg Phe Arg Ser Leu
545                 550                 555                 560

Asp Asp Ser Cys Ser Gln Leu Thr Ser Phe Leu Tyr Ser Phe Cys Gln
                565                 570                 575

Gln Ser Arg Arg Gln Arg Ile Ile Gln Arg Asn Arg Thr Glu Arg Leu
            580                 585                 590

Ser Asp Leu Leu Asp Trp Lys Tyr Leu Gly Arg Tyr Tyr Met Ser Ala
        595                 600                 605

Arg His Met Ala Leu Ser Lys Ala Phe Pro Glu His Phe Thr Tyr Glu
    610                 615                 620

Pro Asn Glu Ala Asp Ala Ala Gln Gly Tyr Arg Tyr Pro Arg Pro Ala
625                 630                 635                 640

Ser Val Pro Pro Ser Pro Ser Leu Ser Arg His Ser Ser Pro His Gln
                645                 650                 655

Ser Glu Asp Glu Glu Asp Pro Arg Asn Gly Pro Leu Glu Glu Asp Gly
            660                 665                 670

Glu Arg Tyr Asp Glu Asp Glu Glu Ala Ala Lys Asp Arg Arg Asn Ile
        675                 680                 685

Arg Ala Pro Glu Trp Pro Arg Arg Ala Ser Cys Thr Ser Ser Thr Ser
    690                 695                 700

Gly Ser Lys Arg Asn Ser Val Asp Thr Ala Thr Ser Ser Ser Leu Ser
705                 710                 715                 720

Thr Pro Ser Glu Pro Leu Ser Pro Thr Ser Ser Leu Gly Glu Glu Arg
                725                 730                 735

Asn


<210> SEQ ID NO 3
<211> LENGTH: 3681
<212> TYPE: DNA
<213> ORGANISM: Mus musculus

<400> SEQUENCE: 3

actgcagctg cccgcccgat tcagtgtctc agctcaccct acctgagtcg gagcgctctg      60

gggcgggggt gcggtcgtgc aataggaagc ggagcgcctt gcaagcttcc cctgggacac     120

ccgctaactc taccggtcac caagtctgct gcgttcccag ccgatctctc tggtttccag     180

ttttggtgct cgaagtcccc tgcccgcagt agccatgcct ctcagccgca gtctctctgt     240

gtcctcgctt ccaggattgg aagactggga ggatgaattc gaccccgaga acgcagtgct     300

tttcgaggtg gcctgggagg tggccaacaa ggtgggtggc atctacactg tgctgcagac     360

gaaggcgaag gtgacagggg atgaatgggg tgacaactac tatctggtgg gaccatacac     420

ggagcagggt gtgaggacgc aggtagagct cctggagccc ccaactccgg aactgaagag     480

gactttggat tccatgaaca gcaagggttg taaggtgtat tttgggcgtt ggctgatcga     540

ggggggaccc ctagtggtgc tcctggatgt aggagcctca gcttgggccc tggagcgctg     600

gaagggtgag ctttgggaca cctgcaacat cggggtaccc tggtacgacc gcgaggccaa     660

tgacgctgtc ctgttcggct tcctcaccac ctggttcctg ggtgagttcc tggcccagaa     720

cgaagagaag ccgtatgtgg ttgcccactt ccacgaatgg ttggctggcg ttggtctgtg     780

tctgtgccgt gcccggcgct tgccggtggc aaccatcttc accactcatg ccacgctgct     840
```

-continued

```
ggggcgctac ctgtgtgctg gcgctgtgga cttctacaac aacctggaga atttcaatgt    900
agacaaggaa gcaggagaga ggcagatcta tcaccggtac tgcatggagc gtgcagcagc    960
tcactgtgcc catgtcttca ctaccgtatc ccagatcacc gcaatcgagg ctcaacacct   1020
ccttaagaga aaaccagata ttgtgacccc caacgggctg aatgtgaaga agttctctgc   1080
tatgcacgaa ttccagaacc ttcatgctca gagcaaagca cgaatccagg aatttgtgcg   1140
tggccatttt tatgggcacc tggacttcaa cctagacaag actttgtatt tctttatcgc   1200
tggccgctat gagttttcca acaagggagc tgatgtgttc ctggaggcat tggcccggct   1260
caactatctg ctcagagtga atggcagtga gcaaacagtt gtcgcattct tcatcatgcc   1320
ggcccggacc aataatttca acgtggaaac cctgaagggc caagccgtgc gcaaacaact   1380
atgggacaca gccaatacag tcaaggagaa atttgggagg aagctctacg aatccctttt   1440
agtggggagc ctcccggaca tgaacaagat gctggacaag gaggacttca ctatgatgaa   1500
gagagccatc tttgccactc agcggcagtc tttcccacca gtgtgcaccc acaacatgct   1560
ggacgactcc tcagacccca tcttgaccac catccgccga attggccttt tcaacagcag   1620
tgccgaccgt gtgaaggtga tttttcaccc agaattcctt tcttccacaa gccctctcct   1680
ccccgtggat tatgaggaat ttgtccgcgg ctgtcacctt ggggtcttcc cctcctacta   1740
tgagccctgg ggctacacac cagcggagtg cactgtcatg ggcatcccca gcatctccac   1800
caacctctcc ggctttggct gctttatgga ggaacacatc gcagatccct cagcttacgg   1860
catttacatt ctggatcgga ggttccgcag cctggatgat tcatgctcac agctcacctc   1920
cttcctgtac agcttctgcc agcagagccg gcgacagcgc atcatccagc ggaaccgcac   1980
agaacggttg tcggacttgc tagattggaa gtacctgggc cggtactaca tgtctgcgcg   2040
ccacatggct ctggccaagg cctttccaga ccacttcacc tatgaacccc atgaggtaga   2100
tgcgacccag ggtaccggt acccacgacc agcctccgtc ccgccgtcgc cctcactgtc   2160
tcgacactcc agcccacacc agagtgagga tgaggaagag ccacgggatg gacccctggg   2220
ggaagacagt gagcgttatg atgaggaaga ggaggctgcc aaggaccgcc gcaacatccg   2280
ggcacctgag tggccacgca gggcctcctg ttcctcctcc acaggtggca gcaagagaag   2340
caactcggtg gacactgggc cctccagctc actcagcaca cccactgagc ccctgagtcc   2400
taccagttcc ctgggtgagg agcgcaacta agctcccacc cccatcccat tccctgcctg   2460
tccagtgctc ctctcgcaga gggcctatgc agatgggagg gtgcctgaac cccactccag   2520
actcttgagt gggaccccta cccagtgtgg tccatagcct aacctctgtt tcagacactc   2580
cagcccttga gctccaatct tggagttccc gcactccacg ccgccgtgcc tttcttggat   2640
tgcaggatgc attctttgtg cactgatctg gagtctccag gcttagactg ggtcccagag   2700
gccaggcatc tgccattgtt tttcaatgcc agaggtttta ggacacctgg tttattggct   2760
tccaggctgt ggcttcttcg tttgatccta taatcataca gagtatgctt tgctcaggcc   2820
tgcctctggg accacctcat gttggattct gtgtggcttc ccgaatcagc caagttcaga   2880
gttaggacat ttcagggatt aacataattg aaaatcagcc tgcaaggtag ctcagtagct   2940
ctgtcgacag attgcttgtc tagcatgccc gaagccctgg gatctaactc tagaacctca   3000
taaacctggt gcggtgatac acatctgtaa tcccagcact cggtaggtag aggtagacgg   3060
atcaagagtt aaaggccatc atcctctgct acatagggag ttcaaggcca aactgggcaa   3120
catgagacac tgtctcaaaa gcaaagtaaa ggtggtggaa tgctcacggt cctccatttc   3180
aacccacgac tgcgatgctg ggacatgctg caaggttggc ctccctgggt gtgttcttca   3240
```

-continued

```
aaggagcatg cggagttgga ccagacacct ttctgccttt tttctggacc agaccttctt   3300

ttccttggtc cagtgtcccc tctagggaat gcctccattg agggcagaat gtctgtcaac   3360

cccacaagtg ctcagcccac tgtgaaacca ctgggttctg ggtcccagtg gctgaatcag   3420

gagtcttttg tcactgtgct gcaccccggt cccctttcct gatacaaaac cgagcccacc   3480

ggcttcttga agccccacat gtacctcgag gcctttctgc ctgcaagctt cagtgaatgg   3540

gcgggcccct cctcacgtgt gctgtgtctg gcccagtgcc tttggtttgc atttgggagg   3600

gggagggcag aaggtgtgtg attggagtgt gtctagagat gaaaaaaaaa aaaagaaaat   3660

acacctgtat ttaagaatgc c                                              3681


<210> SEQ ID NO 4
<211> LENGTH: 738
<212> TYPE: PRT
<213> ORGANISM: Mus musculus

<400> SEQUENCE: 4

Met Pro Leu Ser Arg Ser Leu Ser Val Ser Ser Leu Pro Gly Leu Glu
1               5                   10                  15

Asp Trp Glu Asp Glu Phe Asp Pro Glu Asn Ala Val Leu Phe Glu Val
            20                  25                  30

Ala Trp Glu Val Ala Asn Lys Val Gly Gly Ile Tyr Thr Val Leu Gln
        35                  40                  45

Thr Lys Ala Lys Val Thr Gly Asp Glu Trp Gly Asp Asn Tyr Tyr Leu
    50                  55                  60

Val Gly Pro Tyr Thr Glu Gln Gly Val Arg Thr Gln Val Glu Leu Leu
65                  70                  75                  80

Glu Pro Pro Thr Pro Glu Leu Lys Arg Thr Leu Asp Ser Met Asn Ser
                85                  90                  95

Lys Gly Cys Lys Val Tyr Phe Gly Arg Trp Leu Ile Glu Gly Gly Pro
            100                 105                 110

Leu Val Val Leu Leu Asp Val Gly Ala Ser Ala Trp Ala Leu Glu Arg
        115                 120                 125

Trp Lys Gly Glu Leu Trp Asp Thr Cys Asn Ile Gly Val Pro Trp Tyr
    130                 135                 140

Asp Arg Glu Ala Asn Asp Ala Val Leu Phe Gly Phe Leu Thr Thr Trp
145                 150                 155                 160

Phe Leu Gly Glu Phe Leu Ala Gln Asn Glu Glu Lys Pro Tyr Val Val
                165                 170                 175

Ala His Phe His Glu Trp Leu Ala Gly Val Gly Leu Cys Leu Cys Arg
            180                 185                 190

Ala Arg Arg Leu Pro Val Ala Thr Ile Phe Thr Thr His Ala Thr Leu
        195                 200                 205

Leu Gly Arg Tyr Leu Cys Ala Gly Ala Val Asp Phe Tyr Asn Asn Leu
    210                 215                 220

Glu Asn Phe Asn Val Asp Lys Glu Ala Gly Glu Arg Gln Ile Tyr His
225                 230                 235                 240

Arg Tyr Cys Met Glu Arg Ala Ala Ala His Cys Ala His Val Phe Thr
                245                 250                 255

Thr Val Ser Gln Ile Thr Ala Ile Glu Ala Gln His Leu Leu Lys Arg
            260                 265                 270

Lys Pro Asp Ile Val Thr Pro Asn Gly Leu Asn Val Lys Lys Phe Ser
        275                 280                 285
```

-continued

```
Ala Met His Glu Phe Gln Asn Leu His Ala Gln Ser Lys Ala Arg Ile
    290                 295                 300

Gln Glu Phe Val Arg Gly His Phe Tyr Gly His Leu Asp Phe Asn Leu
305                 310                 315                 320

Asp Lys Thr Leu Tyr Phe Phe Ile Ala Gly Arg Tyr Glu Phe Ser Asn
                325                 330                 335

Lys Gly Ala Asp Val Phe Leu Glu Ala Leu Ala Arg Leu Asn Tyr Leu
            340                 345                 350

Leu Arg Val Asn Gly Ser Glu Gln Thr Val Val Ala Phe Phe Ile Met
        355                 360                 365

Pro Ala Arg Thr Asn Asn Phe Asn Val Glu Thr Leu Lys Gly Gln Ala
    370                 375                 380

Val Arg Lys Gln Leu Trp Asp Thr Ala Asn Thr Val Lys Glu Lys Phe
385                 390                 395                 400

Gly Arg Lys Leu Tyr Glu Ser Leu Leu Val Gly Ser Leu Pro Asp Met
                405                 410                 415

Asn Lys Met Leu Asp Lys Glu Asp Phe Thr Met Met Lys Arg Ala Ile
            420                 425                 430

Phe Ala Thr Gln Arg Gln Ser Phe Pro Pro Val Cys Thr His Asn Met
        435                 440                 445

Leu Asp Asp Ser Ser Asp Pro Ile Leu Thr Thr Ile Arg Arg Ile Gly
    450                 455                 460

Leu Phe Asn Ser Ser Ala Asp Arg Val Lys Val Ile Phe His Pro Glu
465                 470                 475                 480

Phe Leu Ser Ser Thr Ser Pro Leu Leu Pro Val Asp Tyr Glu Glu Phe
                485                 490                 495

Val Arg Gly Cys His Leu Gly Val Phe Pro Ser Tyr Tyr Glu Pro Trp
            500                 505                 510

Gly Tyr Thr Pro Ala Glu Cys Thr Val Met Gly Ile Pro Ser Ile Ser
        515                 520                 525

Thr Asn Leu Ser Gly Phe Gly Cys Phe Met Glu Glu His Ile Ala Asp
    530                 535                 540

Pro Ser Ala Tyr Gly Ile Tyr Ile Leu Asp Arg Arg Phe Arg Ser Leu
545                 550                 555                 560

Asp Asp Ser Cys Ser Gln Leu Thr Ser Phe Leu Tyr Ser Phe Cys Gln
                565                 570                 575

Gln Ser Arg Arg Gln Arg Ile Ile Gln Arg Asn Arg Thr Glu Arg Leu
            580                 585                 590

Ser Asp Leu Leu Asp Trp Lys Tyr Leu Gly Arg Tyr Tyr Met Ser Ala
        595                 600                 605

Arg His Met Ala Leu Ala Lys Ala Phe Pro Asp His Phe Thr Tyr Glu
    610                 615                 620

Pro His Glu Val Asp Ala Thr Gln Gly Tyr Arg Tyr Pro Arg Pro Ala
625                 630                 635                 640

Ser Val Pro Pro Ser Pro Ser Leu Ser Arg His Ser Ser Pro His Gln
                645                 650                 655

Ser Glu Asp Glu Glu Glu Pro Arg Asp Gly Pro Leu Gly Glu Asp Ser
            660                 665                 670

Glu Arg Tyr Asp Glu Glu Glu Glu Ala Ala Lys Asp Arg Arg Asn Ile
        675                 680                 685

Arg Ala Pro Glu Trp Pro Arg Arg Ala Ser Cys Ser Ser Ser Thr Gly
    690                 695                 700

Gly Ser Lys Arg Ser Asn Ser Val Asp Thr Gly Pro Ser Ser Ser Leu
```

-continued

```
705                 710                 715                 720

Ser Thr Pro Thr Glu Pro Leu Ser Pro Thr Ser Ser Leu Gly Glu Glu
                725                 730                 735

Arg Asn


<210> SEQ ID NO 5
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic morpholino oligonucleotide"
<220> FEATURE:
<221> NAME/KEY: modified_base
<222> LOCATION: (1)..(75)
<223> OTHER INFORMATION: Phosphorodiamidate morpholino nucleotide
<220> FEATURE:
<221> NAME/KEY: misc_feature
<222> LOCATION: (1)..(75)
<223> OTHER INFORMATION: /note="This sequence may encompass 5-25
      repeating 'AGC' units"

<400> SEQUENCE: 5

agcagcagca gcagcagcag cagcagcagc agcagcagca gcagcagcag cagcagcagc     60

agcagcagca gcagc                                                      75


<210> SEQ ID NO 6
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic morpholino oligonucleotide"
<220> FEATURE:
<221> NAME/KEY: modified_base
<222> LOCATION: (1)..(75)
<223> OTHER INFORMATION: Phosphorodiamidate morpholino nucleotide
<220> FEATURE:
<221> NAME/KEY: misc_feature
<222> LOCATION: (1)..(75)
<223> OTHER INFORMATION: /note="This sequence may encompass 5-25
      repeating 'GCA' units"

<400> SEQUENCE: 6

gcagcagcag cagcagcagc agcagcagca gcagcagcag cagcagcagc agcagcagca     60

gcagcagcag cagca                                                      75


<210> SEQ ID NO 7
<211> LENGTH: 75
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic morpholino oligonucleotide"
<220> FEATURE:
<221> NAME/KEY: modified_base
<222> LOCATION: (1)..(75)
<223> OTHER INFORMATION: Phosphorodiamidate morpholino nucleotide
<220> FEATURE:
<221> NAME/KEY: misc_feature
<222> LOCATION: (1)..(75)
<223> OTHER INFORMATION: /note="This sequence may encompass 5-25
      repeating 'CAG' units"

<400> SEQUENCE: 7

cagcagcagc agcagcagca gcagcagcag cagcagcagc agcagcagca gcagcagcag     60
```

cagcagcagc agcag 75

<210> SEQ ID NO 8
<211> LENGTH: 2
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 8

Phe Ser
1

<210> SEQ ID NO 9
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 9

Phe Ser Gln
1

<210> SEQ ID NO 10
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 10

Phe Ser Gln Lys
1

<210> SEQ ID NO 11
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: Any amino acid
<220> FEATURE:
<221> NAME/KEY: VARIANT
<222> LOCATION: (3)..(3)
<223> OTHER INFORMATION: /replace="Asp" or "Lys" or "Ser" or "Thr"
<220> FEATURE:
<221> NAME/KEY: MOD_RES
<222> LOCATION: (4)..(4)
<223> OTHER INFORMATION: Beta-Ala
<220> FEATURE:
<221> NAME/KEY: VARIANT
<222> LOCATION: (4)..(4)
<223> OTHER INFORMATION: /replace="Beta-Gly"
<220> FEATURE:
<221> NAME/KEY: misc_feature
<222> LOCATION: (1)..(4)
<223> OTHER INFORMATION: /note="Variant residues given in the sequence have no preference with respect to those in the annotations for variant positions"

<400> SEQUENCE: 11

Phe Xaa Glu Ala
1

<210> SEQ ID NO 12
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 12

Arg Xaa Xaa Xaa Xaa Xaa Arg Arg Arg Xaa Phe Ser Gln Gly
1 5 10

<210> SEQ ID NO 13
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid

```
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 13

Arg Xaa Xaa Xaa Xaa Xaa Xaa Arg Arg Xaa Phe Ser Gln Gly
1               5                   10


<210> SEQ ID NO 14
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 14

Arg Xaa Xaa Xaa Arg Xaa Arg Xaa Arg Xaa Phe Ser Gln Gly
1               5                   10


<210> SEQ ID NO 15
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
```

<221> NAME/KEY: MOD_RES
<222> LOCATION: (4)..(4)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (5)..(5)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 15

Arg Arg Xaa Xaa Xaa Xaa Xaa Xaa Arg Xaa Phe Ser Gln Gly
1               5                   10

<210> SEQ ID NO 16
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (4)..(4)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 16

Arg Arg Arg Xaa Xaa Xaa Xaa Xaa Arg Xaa Phe Ser Gln Gly
1               5                   10

<210> SEQ ID NO 17
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 17

```
Arg Xaa Arg Xaa Xaa Xaa Xaa Xaa Arg Xaa Phe Ser Gln Gly
1               5                   10
```

<210> SEQ ID NO 18
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (3)..(3)
<223> OTHER INFORMATION: cis-2-aminocyclopentane-1-carbonyl or cis-(1R,2S)-2-aminocyclopentane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or 1,3 cis-aminocyclohexane carboxylic acid
<220> FEATURE:
<221> NAME/KEY: MOD_RES -continued
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 18

Arg Arg Xaa Xaa Xaa Xaa Xaa Xaa Arg Xaa Phe Ser Gln Gly
1               5                   10

<210> SEQ ID NO 19
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 19

Arg Xaa Xaa Xaa Xaa Xaa Xaa Xaa Arg Xaa Phe Ser Gln Gly
1               5                   10

<210> SEQ ID NO 20
<211> LENGTH: 14
<212> TYPE: PRT
<213> ORGANISM: Artificial Sequence
<220> FEATURE:
<221> NAME/KEY: source

```
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 20

Arg Xaa Xaa Xaa Xaa Arg Xaa Xaa Arg Xaa Phe Ser Gln Gly
1               5                   10


<210> SEQ ID NO 21
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
```

<223> OTHER INFORMATION: 6-aminohexanoic acid

<400> SEQUENCE: 21

Arg Arg Xaa Arg Xaa Xaa Xaa Xaa Arg Xaa Phe Ser Gln Gly
1 5 10

<210> SEQ ID NO 22
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (3)..(3)
<223> OTHER INFORMATION: cis-2-aminocyclopentane-1-carbonyl or cis-(1R,2S)-2-aminocyclopentane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (6)..(6)
<223> OTHER INFORMATION: cis-2-aminocyclopentane-1-carbonyl or cis-(1R,2S)-2-aminocyclopentane carboxylic acid
<220> FEATURE:
<221> NAME/KEY: MOD_RES
<222> LOCATION: (7)..(7)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 22

Arg Arg Xaa Xaa Xaa Xaa Xaa Xaa Arg Xaa Phe Ser Gln Gly
1 5 10

<210> SEQ ID NO 23
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 23

Arg Xaa Xaa Xaa Xaa Xaa Arg Xaa Arg Xaa
1 5 10

<210> SEQ ID NO 24
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (2)..(2)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (3)..(3)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 24

Arg Xaa Xaa Xaa Xaa Xaa Arg Xaa Arg Xaa
1 5 10

<210> SEQ ID NO 25
<211> LENGTH: 10
<212> TYPE: PRT

```
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 25

Arg Xaa Xaa Xaa Xaa Xaa Arg Xaa Arg Xaa
1               5                   10


<210> SEQ ID NO 26
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (10)..(10)
<223> OTHER INFORMATION: 6-aminohexanoic acid

<400> SEQUENCE: 26

Arg Arg Arg Arg Arg Arg Arg Arg Arg Xaa
1               5                   10


<210> SEQ ID NO 27
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: cis-2-aminocyclopentane-1-carbonyl or
      cis-(1R,2S)-2-aminocyclopentane carboxylic acid
<220> FEATURE:
```

<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 27

```
Arg Xaa Arg Xaa Xaa Xaa Xaa Xaa Arg Xaa
1               5                   10
```

<210> SEQ ID NO 28
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:

<221> NAME/KEY: MOD_RES
<222> LOCATION: (10)..(10)
<223> OTHER INFORMATION: 6-aminohexanoic acid

<400> SEQUENCE: 28

Arg Xaa Xaa Xaa Xaa Xaa Xaa Xaa Arg Xaa
1 5 10

<210> SEQ ID NO 29
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 29

Arg Arg Arg Xaa Xaa Xaa Xaa Xaa Arg Xaa
1 5 10

<210> SEQ ID NO 30
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 30

Arg Xaa Xaa Xaa Xaa Xaa Arg Arg Arg Xaa
1               5                   10

<210> SEQ ID NO 31
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 31

Arg Xaa Xaa Xaa Xaa Xaa Xaa Arg Arg Xaa
1               5                   10

<210> SEQ ID NO 32
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)

```
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 32

Arg Xaa Xaa Xaa Xaa Arg Xaa Xaa Arg Xaa
1               5                   10


<210> SEQ ID NO 33
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 33

Arg Xaa Xaa Xaa Arg Xaa Arg Xaa Arg Xaa
```

-continued 1 5 10

<210> SEQ ID NO 34
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 34

Arg Xaa Arg Xaa Xaa Xaa Xaa Xaa Arg Xaa
1 5 10

<210> SEQ ID NO 35
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 35

Arg Xaa Xaa Xaa Xaa Xaa Xaa Xaa Arg Xaa
1 5 10

<210> SEQ ID NO 36
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (2)..(2)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (4)..(4)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (5)..(5)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 36

Arg Xaa Xaa Xaa Xaa Xaa Xaa Xaa Arg Xaa
1 5 10

<210> SEQ ID NO 37
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (2)..(2)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (6)..(6)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 37

```
Arg Xaa Xaa Xaa Arg Xaa Xaa Arg Arg Xaa
1               5                   10
```

<210> SEQ ID NO 38
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (3)..(3)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
1,3 cis-aminocyclohexane carboxylic acid <220> FEATURE:
<221> NAME/KEY: MOD_RES
<222> LOCATION: (10)..(10)
<223> OTHER INFORMATION: 6-aminohexanoic acid

<400> SEQUENCE: 38

Arg Arg Xaa Xaa Xaa Xaa Arg Xaa Arg Xaa
1               5                   10

<210> SEQ ID NO 39
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (2)..(2)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (5)..(5)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 39

Arg Xaa Xaa Xaa Xaa Xaa Xaa Arg Arg Xaa
1               5                   10

<210> SEQ ID NO 40
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (2)..(2)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
1,3 cis-aminocyclohexane carboxylic acid
<220> FEATURE:

-continued

<221> NAME/KEY: MOD_RES
<222> LOCATION: (4)..(4)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (5)..(5)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 40

Arg Xaa Xaa Xaa Xaa Xaa Xaa Arg Arg Xaa
1 5 10

<210> SEQ ID NO 41
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (3)..(3)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 41

Arg Arg Xaa Arg Xaa Xaa Xaa Xaa Arg Xaa
1 5 10

<210> SEQ ID NO 42
<211> LENGTH: 10
<212> TYPE: PRT
<213> ORGANISM: Artificial Sequence
<220> FEATURE:

-continued

<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (7)..(7)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 42

Arg Xaa Xaa Xaa Xaa Xaa Xaa Xaa Arg Xaa
1               5                   10

<210> SEQ ID NO 43
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES -continued

```
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 43

Arg Xaa Xaa Arg Xaa Xaa Xaa Xaa Arg Xaa
1               5                   10


<210> SEQ ID NO 44
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 44

Arg Xaa Xaa Xaa Xaa Xaa Xaa Xaa Arg Xaa
1               5                   10


<210> SEQ ID NO 45
<211> LENGTH: 10
<212> TYPE: PRT
<213> ORGANISM: Artificial Sequence
<220> FEATURE:
<221> NAME/KEY: source
```

-continued

<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: cis-2-aminocyclopentane-1-carbonyl or cis-(1R,2S)-2-aminocyclopentane carboxylic acid
<220> FEATURE:
<221> NAME/KEY: MOD_RES
<222> LOCATION: (5)..(5)
<223> OTHER INFORMATION: cis-2-aminocyclopentane-1-carbonyl or cis-(1R,2S)-2-aminocyclopentane carboxylic acid
<220> FEATURE:
<221> NAME/KEY: MOD_RES
<222> LOCATION: (6)..(6)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 45

```
Arg Xaa Xaa Xaa Xaa Xaa Xaa Xaa Arg Xaa
1               5                   10
```

<210> SEQ ID NO 46
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: cis-2-aminocyclopentane-1-carbonyl or cis-(1R,2S)-2-aminocyclopentane carboxylic acid
<220> FEATURE:
<221> NAME/KEY: MOD_RES
<222> LOCATION: (3)..(3)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (6)..(6)

<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 46

Arg Xaa Xaa Xaa Xaa Xaa Xaa Arg Arg Xaa
1               5                   10

<210> SEQ ID NO 47
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (7)..(7)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (8)..(8)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 47

Arg Xaa Xaa Xaa Xaa Xaa Xaa Xaa Arg Xaa
1               5                   10

<210> SEQ ID NO 48
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:

Synthetic peptide"
<220> FEATURE:
<221> NAME/KEY: MOD_RES
<222> LOCATION: (2)..(2)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 48

Arg Xaa Arg Xaa Xaa Arg Xaa Xaa Arg Xaa
1 5 10

<210> SEQ ID NO 49
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (3)..(3)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (5)..(5)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (6)..(6)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 49

Arg Arg Xaa Xaa Xaa Xaa Xaa Xaa Arg Xaa
1               5                   10

<210> SEQ ID NO 50
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (2)..(2)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 50

Arg Xaa Xaa Xaa Xaa Xaa Xaa Xaa Arg Xaa
1               5                   10

<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: MOD_RES
<222> LOCATION: (3)..(3)
<223> OTHER INFORMATION: cis-2-aminocyclopentane-1-carbonyl or cis-(1R,2S)-2-aminocyclopentane carboxylic acid
<220> FEATURE:
<221> NAME/KEY: MOD_RES
<222> LOCATION: (4)..(4)
<223> OTHER INFORMATION: 3-cis-aminocyclohexane or 1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 51

Arg Arg Xaa Xaa Xaa Xaa Xaa Xaa Arg Xaa
1 5 10

<210> SEQ ID NO 52
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: MOD_RES
<222> LOCATION: (3)..(3)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (5)..(5)
<223> OTHER INFORMATION: cis-2-aminocyclopentane-1-carbonyl or
cis-(1R,2S)-2-aminocyclopentane carboxylic acid
<220> FEATURE:
<221> NAME/KEY: MOD_RES
<222> LOCATION: (6)..(6)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (7)..(7)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (8)..(8)
<223> OTHER INFORMATION: 3-cis-aminocyclohexane or
1,3 cis-aminocyclohexane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 52

Arg Arg Xaa Xaa Xaa Xaa Xaa Xaa Arg Xaa
1 5 10

```
<210> SEQ ID NO 53
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (2)..(2)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (3)..(3)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (4)..(4)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (5)..(5)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (6)..(6)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (7)..(7)
<223> OTHER INFORMATION: 3-cis-aminocyclohexane or
      1,3 cis-aminocyclohexane carboxylic acid
<220> FEATURE:
<221> NAME/KEY: MOD_RES
<222> LOCATION: (8)..(8)
<223> OTHER INFORMATION: cis-2-aminocyclopentane-1-carbonyl or
      cis-(1R,2S)-2-aminocyclopentane carboxylic acid
<220> FEATURE:
<221> NAME/KEY: MOD_RES
<222> LOCATION: (10)..(10)
<223> OTHER INFORMATION: 6-aminohexanoic acid

<400> SEQUENCE: 53

Arg Xaa Xaa Xaa Xaa Xaa Xaa Xaa Arg Xaa
1               5                   10


<210> SEQ ID NO 54
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 54

tcagggttgt ggactcaatc atgcc                                           25


<210> SEQ ID NO 55
<211> LENGTH: 25
<212> TYPE: DNA
<213> ORGANISM: Artificial Sequence
<220> FEATURE:
<221> NAME/KEY: source
```

-continued

<223> OTHER INFORMATION: /note="Description of Artificial Sequence:
      Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 55
aaggaccagg gtaagactag ggact 25

<210> SEQ ID NO 56
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 56
gtcctggaca aggattgctg accat 25

<210> SEQ ID NO 57
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 57
ctgcttcctt gtctacattg aactg 25

<210> SEQ ID NO 58
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 58
atacccggcc caggtacttc caatc 25

<210> SEQ ID NO 59
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 59
ctggacaagg attgctgacc atagt 25

<210> SEQ ID NO 60
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 60
aattcatcct cccagtcttc caatc 25

<210> SEQ ID NO 61
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 61
tcccaccgag caggccttac tctga 25

<210> SEQ ID NO 62
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 62
gaccacagct cagaccctac ctggt 25

<210> SEQ ID NO 63
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence: Synthetic morpholino oligonucleotide"
<220> FEATURE:
<221> NAME/KEY: modified_base
<222> LOCATION: (1)..(25)
<223> OTHER INFORMATION: Phosphorodiamidate morpholino nucleotide

<400> SEQUENCE: 63
tcactgtctg gctcacatac ccata 25

<210> SEQ ID NO 64
<211> LENGTH: 11

<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: misc_feature
<222> LOCATION: (1)..(2)
<223> OTHER INFORMATION: /note="Residues at these positions are
non-consecutive and are separated by a NH-(CHR1)n-C(O)- moiety"
<220> FEATURE:
<221> NAME/KEY: MOD_RES
<222> LOCATION: (1)..(1)
<223> OTHER INFORMATION: Arg or D-Arg
<220> FEATURE:
<221> NAME/KEY: MOD_RES
<222> LOCATION: (2)..(2)
<223> OTHER INFORMATION: Arg or D-Arg
<220> FEATURE:
<221> NAME/KEY: MOD_RES
<222> LOCATION: (3)..(3)
<223> OTHER INFORMATION: Arg or D-Arg
<220> FEATURE:
<221> NAME/KEY: MOD_RES
<222> LOCATION: (4)..(4)
<223> OTHER INFORMATION: Beta-Ala
<220> FEATURE:
<221> NAME/KEY: MOD_RES
<222> LOCATION: (5)..(5)
<223> OTHER INFORMATION: Arg or D-Arg
<220> FEATURE:
<221> NAME/KEY: misc_feature
<222> LOCATION: (6)..(7)
<223> OTHER INFORMATION: /note="Residues at these positions are
non-consecutive and are separated by a NH-(CHR1)n-C(O)- moiety"
<220> FEATURE:
<221> NAME/KEY: MOD_RES
<222> LOCATION: (6)..(6)
<223> OTHER INFORMATION: Arg or D-Arg
<220> FEATURE:
<221> NAME/KEY: MOD_RES
<222> LOCATION: (7)..(7)
<223> OTHER INFORMATION: Arg or D-Arg
<220> FEATURE:
<221> NAME/KEY: MOD_RES
<222> LOCATION: (8)..(8)
<223> OTHER INFORMATION: Arg or D-Arg
<220> FEATURE:
<221> NAME/KEY: MOD_RES
<222> LOCATION: (9)..(9)
<223> OTHER INFORMATION: Beta-Ala
<220> FEATURE:
<221> NAME/KEY: misc_feature
<222> LOCATION: (10)..(11)
<223> OTHER INFORMATION: /note="Residues at these positions are
non-consecutive and are separated by a NH-(CHR1)n-C(O)- moiety"
<220> FEATURE:
<221> NAME/KEY: MOD_RES
<222> LOCATION: (10)..(10)
<223> OTHER INFORMATION: Arg or D-Arg
<220> FEATURE:
<221> NAME/KEY: MOD_RES
<222> LOCATION: (11)..(11)
<223> OTHER INFORMATION: Beta-Ala

<400> SEQUENCE: 64

Arg Arg Arg Ala Arg Arg Arg Arg Ala Arg Ala
1               5                   10

<210> SEQ ID NO 65
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:

Synthetic primer"

<400> SEQUENCE: 65
ctggcgctgt ggacttcta 19

<210> SEQ ID NO 66
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 66
acactggtgg gaaagactgc 20

<210> SEQ ID NO 67
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 67
ccagcttgac aagttcgaca 20

<210> SEQ ID NO 68
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 68
aaacacccca aggtgacaac 20

<210> SEQ ID NO 69
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 69
agccatgtac gtagccatcc 20

<210> SEQ ID NO 70
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic primer"

<400> SEQUENCE: 70
ctctcagctg tggtggtgaa 20

<210> SEQ ID NO 71
<211> LENGTH: 9

-continued

<212> TYPE: PRT
<213> ORGANISM: Artificial Sequence
<220> FEATURE:
<221> NAME/KEY: source
<223> OTHER INFORMATION: /note="Description of Artificial Sequence:
Synthetic peptide"
<220> FEATURE:
<221> NAME/KEY: misc_feature
<222> LOCATION: (1)..(2)
<223> OTHER INFORMATION: /note="Residues at these positions are
non-consecutive and are separated by a NH-(CHR1)n-C(O)- moiety"
<220> FEATURE:
<221> NAME/KEY: MOD_RES
<222> LOCATION: (1)..(1)
<223> OTHER INFORMATION: Arg or D-Arg
<220> FEATURE:
<221> NAME/KEY: MOD_RES
<222> LOCATION: (2)..(2)
<223> OTHER INFORMATION: Arg or D-Arg
<220> FEATURE:
<221> NAME/KEY: misc_feature
<222> LOCATION: (3)..(4)
<223> OTHER INFORMATION: /note="Residues at these positions are
non-consecutive and are separated by a NH-(CHR1)n-C(O)- moiety"
<220> FEATURE:
<221> NAME/KEY: MOD_RES
<222> LOCATION: (3)..(3)
<223> OTHER INFORMATION: Arg or D-Arg
<220> FEATURE:
<221> NAME/KEY: MOD_RES
<222> LOCATION: (4)..(4)
<223> OTHER INFORMATION: Arg or D-Arg
<220> FEATURE:
<221> NAME/KEY: misc_feature
<222> LOCATION: (5)..(6)
<223> OTHER INFORMATION: /note="Residues at these positions are
non-consecutive and are separated by a NH-(CHR1)n-C(O)- moiety"
<220> FEATURE:
<221> NAME/KEY: MOD_RES
<222> LOCATION: (5)..(5)
<223> OTHER INFORMATION: Arg or D-Arg
<220> FEATURE:
<221> NAME/KEY: MOD_RES
<222> LOCATION: (6)..(6)
<223> OTHER INFORMATION: Arg or D-Arg
<220> FEATURE:
<221> NAME/KEY: misc_feature
<222> LOCATION: (7)..(8)
<223> OTHER INFORMATION: /note="Residues at these positions are
non-consecutive and are separated by a NH-(CHR1)n-C(O)- moiety"
<220> FEATURE:
<221> NAME/KEY: MOD_RES
<222> LOCATION: (7)..(7)
<223> OTHER INFORMATION: Arg or D-Arg
<220> FEATURE:
<221> NAME/KEY: misc_feature
<222> LOCATION: (8)..(9)
<223> OTHER INFORMATION: /note="Residues at these positions are
non-consecutive and are separated by a NH-(CHR1)n-C(O)- moiety"
<220> FEATURE:
<221> NAME/KEY: MOD_RES
<222> LOCATION: (8)..(8)
<223> OTHER INFORMATION: Arg or D-Arg
<220> FEATURE:
<221> NAME/KEY: MOD_RES
<222> LOCATION: (9)..(9)
<223> OTHER INFORMATION: Beta-Ala

<400> SEQUENCE: 71

Arg Arg Arg Arg Arg Arg Arg Arg Ala
1 5